(12) United States Patent
Shariat et al.

(10) Patent No.: US 11,284,826 B2
(45) Date of Patent: Mar. 29, 2022

(54) METHODS FOR IDENTIFYING WAVE BREAK DURING ATRIAL FIBRILLATION

(71) Applicants: Queen's University at Kingston, Kingston (CA); Kingston Health Sciences Centre, Kingston (CA)

(72) Inventors: Mohammad Hassan Shariat, Kingston (CA); Damian P. Redfearn, Kingston (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 344 days.

(21) Appl. No.: 16/122,978

(22) Filed: Sep. 6, 2018

(65) Prior Publication Data

US 2019/0069792 A1    Mar. 7, 2019

Related U.S. Application Data

(60) Provisional application No. 62/544,691, filed on Sep. 6, 2017.

(51) Int. Cl.
*A61B 5/04* (2006.01)
*A61B 5/042* (2006.01)
(Continued)

(52) U.S. Cl.
CPC .............. *A61B 5/316* (2021.01); *A61B 5/339* (2021.01); *A61B 5/341* (2021.01); *A61B 5/361* (2021.01);
(Continued)

(58) Field of Classification Search
CPC .............. A61B 5/0006; A61B 5/04011; A61B 5/04014; A61B 5/04017; A61B 5/044;
(Continued)

(56) References Cited

U.S. PATENT DOCUMENTS

| 2013/0274582 | A1* | 10/2013 | Afonso | A61B 5/0044 600/374 |
| 2014/0207013 | A1* | 7/2014 | Lian | A61N 1/3702 600/523 |

(Continued)

OTHER PUBLICATIONS

Shariat, M.H. et al., "Regional Dominant Frequency: A New Tool for Wave Break Identification During Atrial Fibrillation," Frontiers in Cardiovascular Medicine. vol. 5, 2018.
(Continued)

*Primary Examiner* — Jennifer Pitrak McDonald
*Assistant Examiner* — Pamela M. Bays
(74) *Attorney, Agent, or Firm* — Stephen J. Scribner

(57) ABSTRACT

Study of intracardiac electrograms (IEGMs) during atrial fibrillation (AF) provides clinically significant information that can be used in ablation therapy. Methods include determining a regional feature, e.g., dominant frequency (RDF), which encompasses the relationship between simultaneously recorded electrodes and identifies the feature components of a region, rather than the feature of a single electrode. Methods employing the regional feature may be used to identify and characterize variation and disorganization in wavefront propagation or wave breaks (WBs) at each recording site, and may be used to direct catheter ablation therapy.

22 Claims, 15 Drawing Sheets

(51) Int. Cl.

| | |
|---|---|
| *A61B 5/046* | (2006.01) |
| *A61B 18/14* | (2006.01) |
| *A61B 5/00* | (2006.01) |
| *A61B 5/316* | (2021.01) |
| *A61B 5/339* | (2021.01) |
| *A61B 5/341* | (2021.01) |
| *A61B 5/361* | (2021.01) |
| *A61B 18/00* | (2006.01) |
| *A61B 17/00* | (2006.01) |
| *A61B 5/283* | (2021.01) |
| *A61B 5/363* | (2021.01) |

(52) U.S. Cl.
CPC ............ *A61B 5/0006* (2013.01); *A61B 5/283* (2021.01); *A61B 5/363* (2021.01); *A61B 5/7203* (2013.01); *A61B 5/7225* (2013.01); *A61B 5/7257* (2013.01); *A61B 18/1492* (2013.01); *A61B 2017/00053* (2013.01); *A61B 2018/00351* (2013.01); *A61B 2018/00839* (2013.01); *A61B 2505/05* (2013.01)

(58) Field of Classification Search
CPC ..... A61B 5/046; A61B 5/0464; A61B 5/7203; A61B 5/7225; A61B 2017/00053; A61B 2018/00351
See application file for complete search history.

(56) References Cited

U.S. PATENT DOCUMENTS

| | | | | |
|---|---|---|---|---|
| 2014/0336520 | A1* | 11/2014 | Zeng | A61N 7/00 600/516 |
| 2017/0065198 | A1* | 3/2017 | Ruppersberg | A61B 5/316 |
| 2017/0079542 | A1* | 3/2017 | Spector | A61B 5/287 |

OTHER PUBLICATIONS

Shariat, M. H. et al., "Bipolar Intracardiac Electrogram Active Interval Extraction During Atrial Fibrillation" IEEE Transactions on Biomedical Engineering, vol. 64, No. 9, pp. 2122-2133, 2017.
Shariat, M. H., et al., "Activation Detection of Intracardiac Electrogram During Atrial Fibrillation Based on the Variance Equality Test," 28th IEEE Canadian Conference on Electrical and Computer Engineering (CCECE), pp. 387-391. May 2015.
Shariat, M.H., "Processing the Intracardiac Electrogram for Atrial Fibrillation Ablation." Ph.D., thesis, Queen's University, Canada (2016).
Shariat, M,H, et al., "Sequential regional dominant frequency mapping during atrial fibrillation: a novel thechnique." Can J Cardiol. (2016) 32:S181-2. doi: 10.1016/j.cjca.2016.07.284.
Rogers, J.M., et al., "A Collocation-Galerkin Finite Element Model of Cardiac Action Potential Propagation," IEEE Transactions on Biomedical Engineering, vol. 41, No. 8, pp. 743-757, (1994).
Pertsov, A.M., et al., "Spiral Waves of Excitation Underlie Reentrant Activity in Isolated Cardiac Muscle." Circulation research, vol. 72, No. 3, pp. 631-650, (1993).
Jacquemet, V. et al., "Study of unipolar electrogram morphology in a computer model of atrial fibrillation," Journal of cardiovascular electrophysiology, vol. 14, No. s10, 2003.
Verma, A. et al., "A prospective, multicenter evaluation of ablating complex fractionated electrograms (CFEs) during atrial fibrillation (AF) identified by an automated mapping algorithm: Acute effects on AF and efficacy as an adjuvant strategy," Heart Rhythm, vol. 5, No. 2, pp. 198-205, (2008).
Nademanee, K. et al., "How to perform electrogram-guided atrial fibrillation ablation," Heart Rhythm, vol. 3. No. 8, pp. 981-984, (2006).
Atienza, F. et al., "Real-time dominant frequency mapping and ablation of dominant frequency sites in atrial (fibrillation with left-to-right frequency gradients predicts long-term maintenance of sinus rhythm," Heart Rhythm, vol. 6, No. 1, pp. 33-40, (2009).
Atienza, F. et al., "Comparison of Radiofrequency Catheter Ablation of Drivers and Circumferential Pulmonary Vein Isolation in Atrial Fibrillation: A Noninferiority Randomized Multicenter RADAR-AF Trial," Journal of the American College of Cardiology, vol. 64, No. 23, pp. 2455-2467, (2014).
Porter, M. et al., "Prospective Study of Atrial Fibrillation Termination During Ablation Guided by Automated Detection of Fractionated Electrograms," Journal of cardiovascular electrophysiology, vol. 19, No. 6, pp. 613-620, (2008).
Jarman, J.W., et al., "Organizational Index Mapping to Identify Focal Sources During Persistent Atrial Fibrillation," Journal of cardiovascular electrophysiology, vol. 25, No. 4, pp. 355-363, (2014).
Haissaguerre, M., et al., "Driver Domains in Persistent Atrial Fibrillation," Circulation, pp. 530-538, (2014).
Berntsen, R.F., et al., "Focal impulse and rotor modulation as a stand-alone procedure for the treatment of paroxysmal atrial fibrillation: A within-patient controlled study with implanted cardiac monitoring," Heart Rhythm, vol. 13, No. 9, pp. 1768-1774, (2016).
Morillo, C.A., et al., "Radiofrequency Ablation vs Antiarhythmic Drugs as First-Line Treatment of Paroxysmal Atrial Fibrillation (RAAFT-2): A Randomized Trial," Jama, vol. 311, No. 7, pp. 692-700, (2014).
Verma, A., et al., "Approaches to Catheter Ablation for Persistent Atrial Fibrillation," New England Journal of Medicine, vol. 372, No. 19, pp. 1812-1822, (2015).
Ng. J. et al., "Effect of electrogram characteristics on the relationship of dominant frequency to atrial activation rate in atrial fibrillation." Heart Rhythm, vol. 3, No. 11, pp. 1295-1305, (2006).
Ng. J. et al., "Technical Considerations for Dominant Frequency Analysis," Journal of Cardiovascular Electrophysiology, vol. 18, No. 7, pp. 757-764, (2007).
Verma, A., et al., "Relationship Between Complex Fractionated Electrograms (CFE) and Dominant Frequency (DF) Sites and Prospective Assessment of Adding DF-Guided Ablation to Pulmonary Vein Isolation in Persistent Atrial Fibrillation (AF)," J. of Card, Electrophysiology, vol. 22, No. 12, pp. 1309-1316, (2011).
Climent, A.M., et al., "High Resolution Microscopic Optical Mapping of Anatomical and Functional Reentries in Human Cardiac Cell Cultures," in IEEE Computing in Cardiology Conference (CinC), pp. 233-236, (2016).
Jalife, J. et al., "Mother rotors and fibrillatory conduction: a mechanism of atrial fibrillation," Cardiovascular research, vol. 54, No. 2, pp. 204-216, (2002).
Morillo, C.A., et al., "Chronic Rapid Atrial Pacing Structural, Functional, and Electrophysiological Characteristics of a New Model of Sustained Atrial Fibrillation," Circulation, vol. 91, No. 5, pp. 1588-1595, (1995).
Singh, S.M. et al., "Intraprocedural Use of Ibutilide to Organize and Guide Ablation of Complex Fractionated Atrial Electrograms: Preliminary assessment of a modified step-wise approach to ablation of persistent atrial fibrillation," Journal of cardiovascular electrophysiology, vol. 21, No. 6, pp. 608-616, (2018).

* cited by examiner

Spiral Core Trajectory

METHODS FOR IDENTIFYING WAVE BREAK DURING ATRIAL FIBRILLATION

RELATED APPLICATION

This application claims the benefit of the filing date of Application No. 62/554,691, filed Sep. 6, 2017, the contents of which are incorporated herein by reference in their entirety.

FIELD

The invention relates to methods for analyzing intracardiac electrogram (IEGM) data obtained during atrial fibrillation (AF) and ventricular fibrillation to detect a feature, and using the detected feature as a basis for treatment of AF. More particularly, methods may include determining a regional feature, such as regional dominant frequency (RDF), which may be used to identify and characterize variation and disorganization in wavefront propagation or wave break (WB) at each electrode site, and may be used to direct catheter ablation therapy.

BACKGROUND

Atrial fibrillation (AF) is the most common arrhythmia and a primary cause of stroke. It is characterized by a mosaic of heterogeneous spatiotemporal wavefront propagation that results in complex signal formation and fragmentation. Catheter ablation therapy is a method for treatment of AF which involves targeting and elimination of putative triggers and perpetuating sources found in pulmonary veins and elsewhere in the atria utilizing electroanatomic information.

Information extracted from intracardiac electrograms (IEGMs) collected from both atria, e.g., relative timing of pulmonary vein potentials, duration of bipolar electrograms [5], complex fractionated electrograms (CFE) [6,7] and the dominant frequency (DF) [8], are often used to guide ablation therapy procedures. Feature analyses of IEGMs are based on the time and frequency analysis of the recorded signals from individual bipolar/unipolar electrodes of a conventional multi-electrode recording catheter, i.e., the IEGM of each electrode is processed and used to estimate the CFE or DF. After processing the recorded IEGM, a CFE or DF value is assigned to each electrode at an XYZ coordinate location. The assigned values are further processed, interpolated, and colour-coded to generate an anatomical map of the cardiac chamber to aid targeting of catheter ablation and thus improve procedural efficacy [6,9, 10]. Since the IEGM of each electrode of the catheter is processed independently of other simultaneously recorded electrodes, these conventional methods do not provide any information about the wavefront propagation during AF [11]. Indeed, mapping of fractionated signals has not delivered success due to confounding causes, such as wavefront collision, resulting in high frequency and complex electrograms. Recent studies suggest the CFE strategy appears no better than empiric ablation [15]. Experimental work has suggested high frequency electrograms are located at sources of AF, these sources are surrounded by continuous WB, potentially obscuring the driver [20].

Methods to compensate for the deficiencies of independent IEGM analysis approaches have met with debate and variable results, or are acquired from a surface ECG and are thus limited in spatial resolution and application [12,13]. The underlying mechanisms for AF remain elusive, and outcomes remain suboptimal in both paroxysmal [14] and persistent AF [15]. Thus, there is a need to better understand the complex mechanisms involved in AF perpetuation.

SUMMARY

According to one aspect of the invention there is provided a method for detecting an abnormality in wavefront propagation during cardiac atrial fibrillation in a subject, comprising: extracting one or more feature from intracardiac electrograms of one or more electrodes disposed in a sampled region to determine a regional feature; using time-frequency analysis of the regional feature to detect spatiotemporal heterogeneity in the regional feature and a change in wavefront dynamics; wherein spatiotemporal heterogeneity in the regional feature and wavefront dynamics in the sampled region indicate an abnormality in wavefront propagation in the subject.

In various embodiments, the one or more extracted feature is at least one of electrogram active interval envelope, number of baseline occurrence (NO), isoelectric line portion, instantaneous power, and Shannon entropy. Extracted features may be combined to extract the regional feature. In some embodiments, two or more extracted features may be combined to extract the regional feature. The two or more extracted features may be combined using weighted averaging to extract the regional feature.

In one embodiment, the method further comprises signal exclusion. Signal exclusion may comprise one or more of exclusion of a physiologically irrelevant signal, exclusion of electrodes with low signal to noise ratio; and exclusion of an electrogram collected at a distance too far from the atrial surface (i.e., non-contact).

In one embodiment, the method further comprises outputting results graphically. Outputting results may comprise colour coding on a three-dimensional (3D) map of the sampled region.

In one embodiment, the regional feature is a regional dominant frequency (RDF).

In one embodiment, the abnormality in wavefront propagation in the sampled region identifies a source of cardiac atrial fibrillation in the subject. The method may include using the source of cardiac atrial fibrillation to determine a location of ablation therapy in the subject.

In one embodiment, the method comprises detecting a change in wavefront dynamics comprises: determining an instantaneous RDF (iRDF) corresponding to a short time window; and identifying a wave break (WB) in the iRDF.

In one embodiment, the method comprises identifying a WB based on one or more of: a drop in iRDF that is at least $f_{th0}$ Hz below the RDF; a drop in iRDF that is below $f_{th1}$ Hz; and a duration of at least $T_{th}$ ms; where $f_{th0}$, $f_{th1}$, $T_{th}$ are user defined values.

In one embodiment, the method comprises determining the RDF based on using an intracardiac electrogram data segment of at least four seconds duration.

In one embodiment, the method comprises determining wave break rate (WBR) to characterize wavefront propagation; wherein WBR is determined based on an IEGM data segment of at least 25 seconds duration.

In one embodiment, the method comprises determining a wave break measure to characterize wavefront propagation; wherein the wave break measure is selected from a WBR that describes a number of WBs per second, a longest WB duration throughout a recording time, average or shortest time between consecutive WBs, or WB duration percentage; wherein WB duration percentage is the total WB duration divided by IEGM segment duration.

In one embodiment, the method comprises detecting a change in wavefront dynamics relative to the RDF for the sampled region by selecting a short time window of 0.5-3.0 s.

In one embodiment, the method comprises detecting a change in wavefront dynamics relative to the RDF for the sampled region by selecting a short time window of 1 s or less.

In one embodiment, the method comprises detecting a change in wavefront dynamics relative to the RDF for the sampled region by selecting a short time window of 2 s or less.

In one embodiment, the method comprises displaying a colour-coded map to highlight one or more critical site; wherein a critical site is characterized by a site with high RDF and low WBR, a site with high WBR and low amplitude, and a site with WBR higher than a selected threshold. In other embodiments, different combinations of regional features may be used. For example, critical sites may be sites with high RDF and high WB duration percentage.

According to another aspect of the invention there is provided programmed media for use with a processor, comprising: a code stored on non-transitory storage media compatible with the processor, the code containing instructions to direct the processor to receive IEGM data corresponding to a plurality of IEGMs from electrodes, and carry out one or more processing steps according to FIG. 1A, FIG. 1B, and/or FIG. 1C.

In one embodiment, the programmed includes a code stored on non-transitory storage media compatible with the processor, the code containing instructions to direct the processor to: receive an intracardiac electrogram of one or more electrodes disposed in a sampled region of a subject; extract one or more feature from the intracardiac electrogram to determine a regional feature; use time-frequency/scale analysis of the regional feature to detect spatiotemporal heterogeneity in the regional feature and a change in wavefront dynamics; wherein spatiotemporal heterogeneity in the regional feature and wavefront dynamics in the sampled region indicate an abnormality in wavefront propagation in the subject; and output a result including a location of sources of cardiac atrial fibrillation in the subject.

BRIEF DESCRIPTION ON THE DRAWINGS

For a greater understanding of the invention, and to show more clearly how it may be carried into effect, embodiments will be described, by way of example, with reference to the accompanying drawings, wherein.

Figures 2A, 2B, 2C:
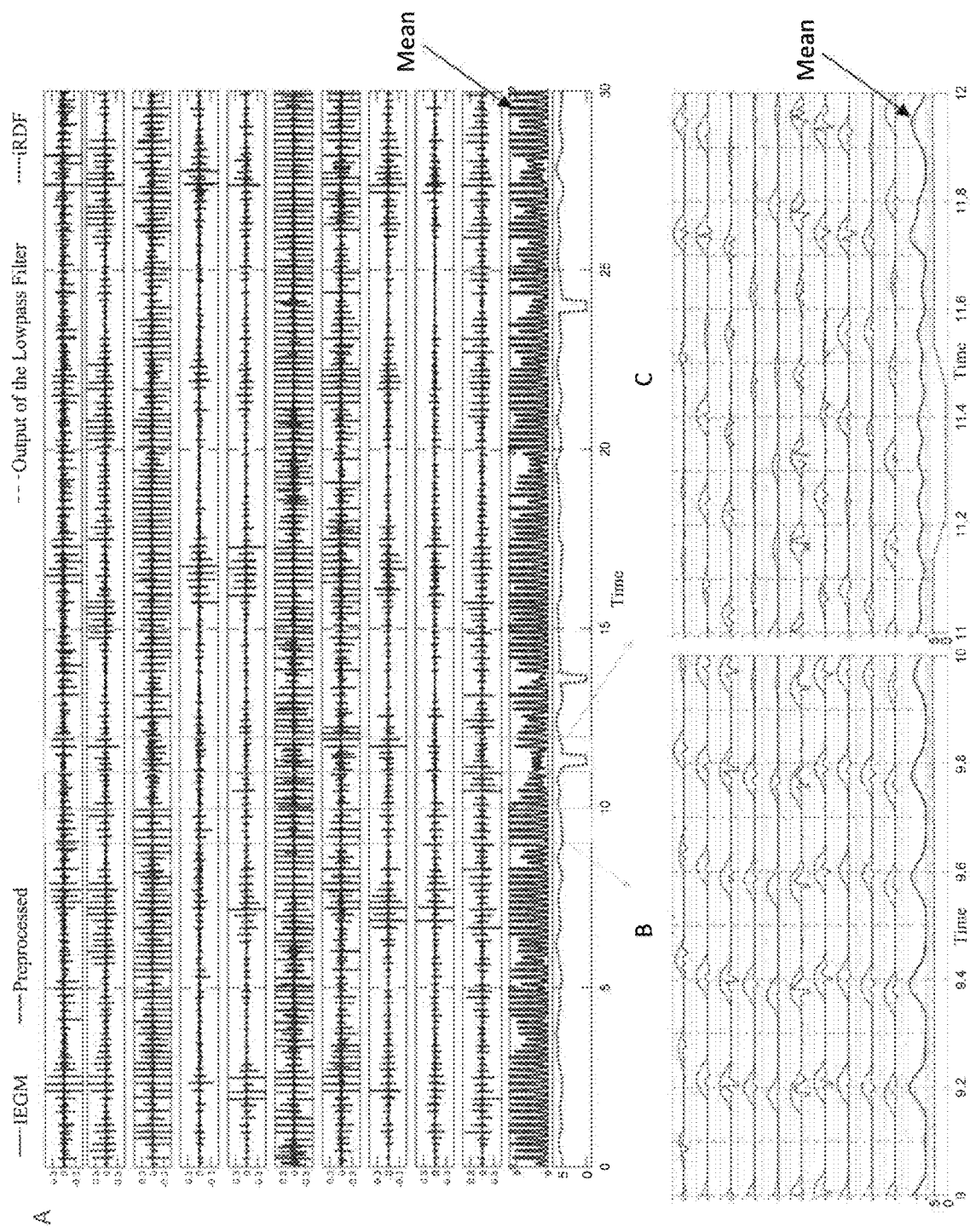

FIG. 2A shows bipolar intracardiac electrograms (IEGMs) collected from a patient with persistent AF (from top to bottom, axes 1 to 10). The average of the preprocessed signals and the low pass filtered average are plotted on the 11$^{th}$ axis, and the 12$^{th}$ axis shows the dominant frequency (DF) of the low pass filtered signal. FIG. 2B shows the IEGM segment with clear wavefronts, and the normalized preprocessed signals (with the maximum amplitude of one) are also plotted. The output of the low pass filter has a large peak for each wavefront and the DF for this figure varies between 4.9 to 5.5 Hz. FIG. 2C shows another segment of the IEGM with a wave break in which there are no distinguishable wavefronts at the beginning of the segment. Here, the average of the preprocessed signal has multiple small peaks that are not present when low pass filtered, and there is a significant drop in the instantaneous regional dominant frequency (iRDF) at this time.

Figure 3:
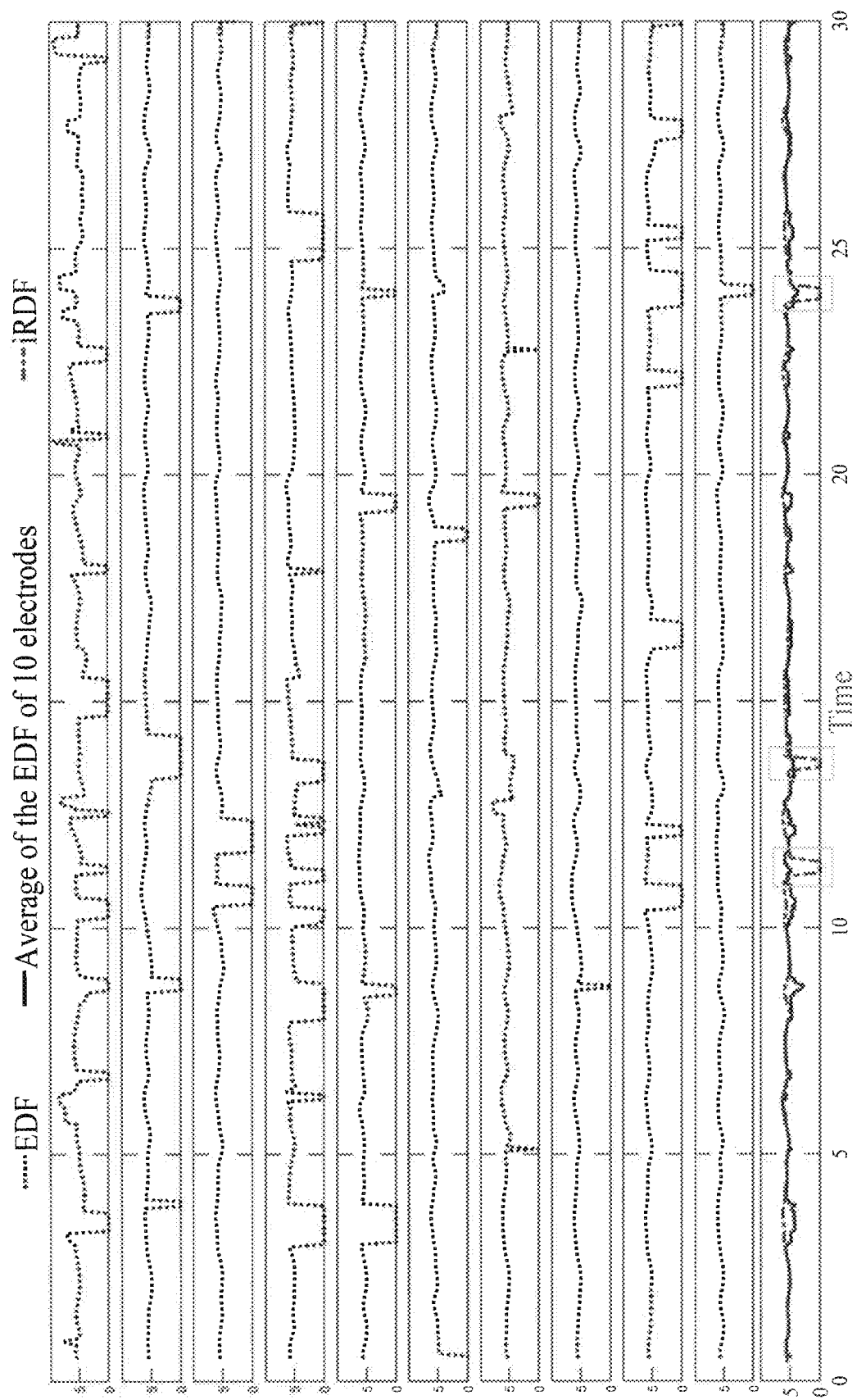

FIG. 3 is a plot showing electrode dominant frequency (EDF) and instantaneous regional dominant frequency (iRDF) of the IEGM shown in FIG. 2A when T=1 s. The average of the EDF of all the electrodes (shown in solid line) does not drop at the same time as the iRDF, identifying different wave break (WB) instances. Boxes mark WB instances obtained using RDF.

Figure 4:
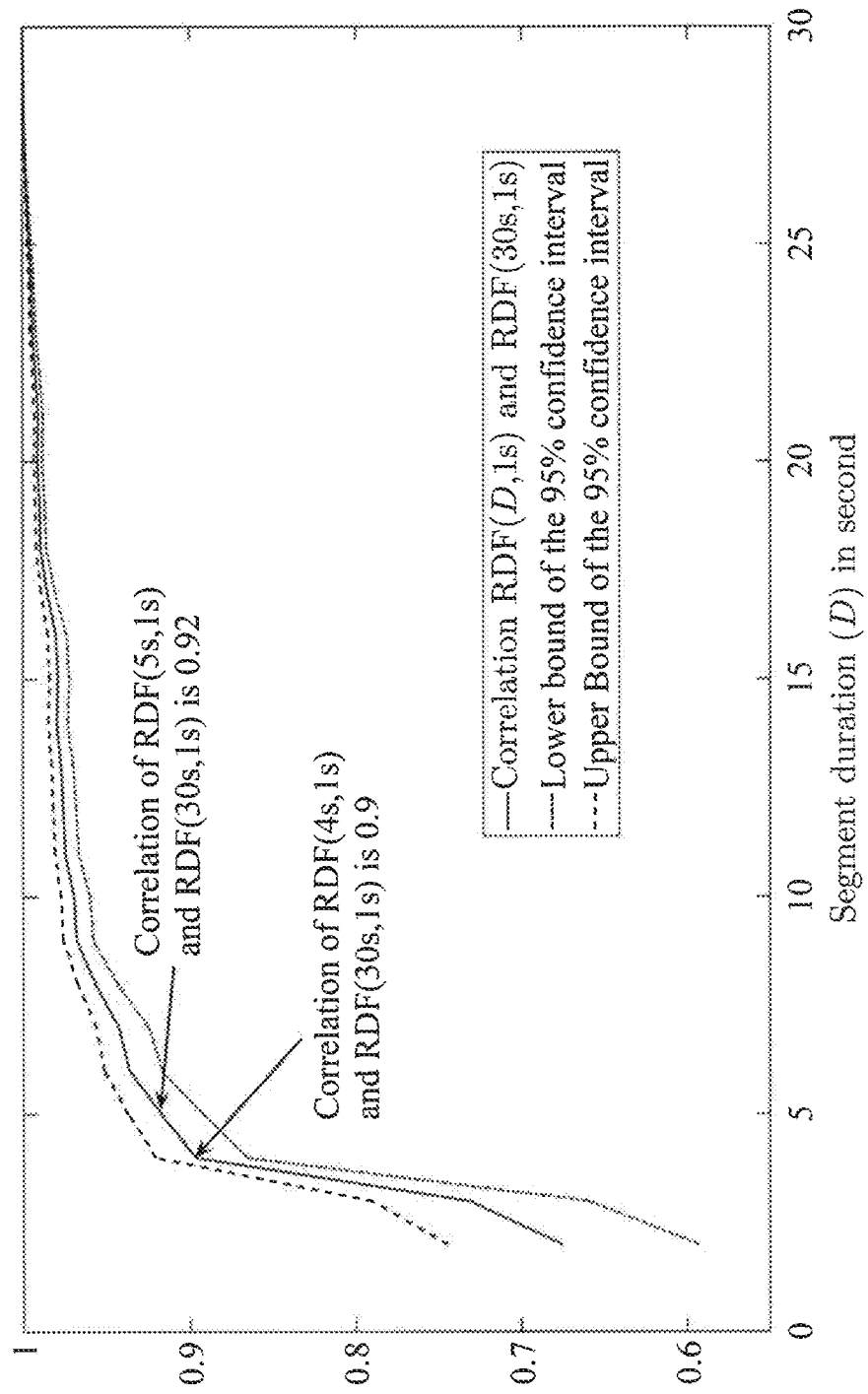

FIG. 4 is a plot showing the Pearson correlation of the RDF (D, 1 s) and RDF (30 s, 1 s), with the upper and lower bounds of the confidence interval of the correlation as a function of segment duration D.

Figure 5:
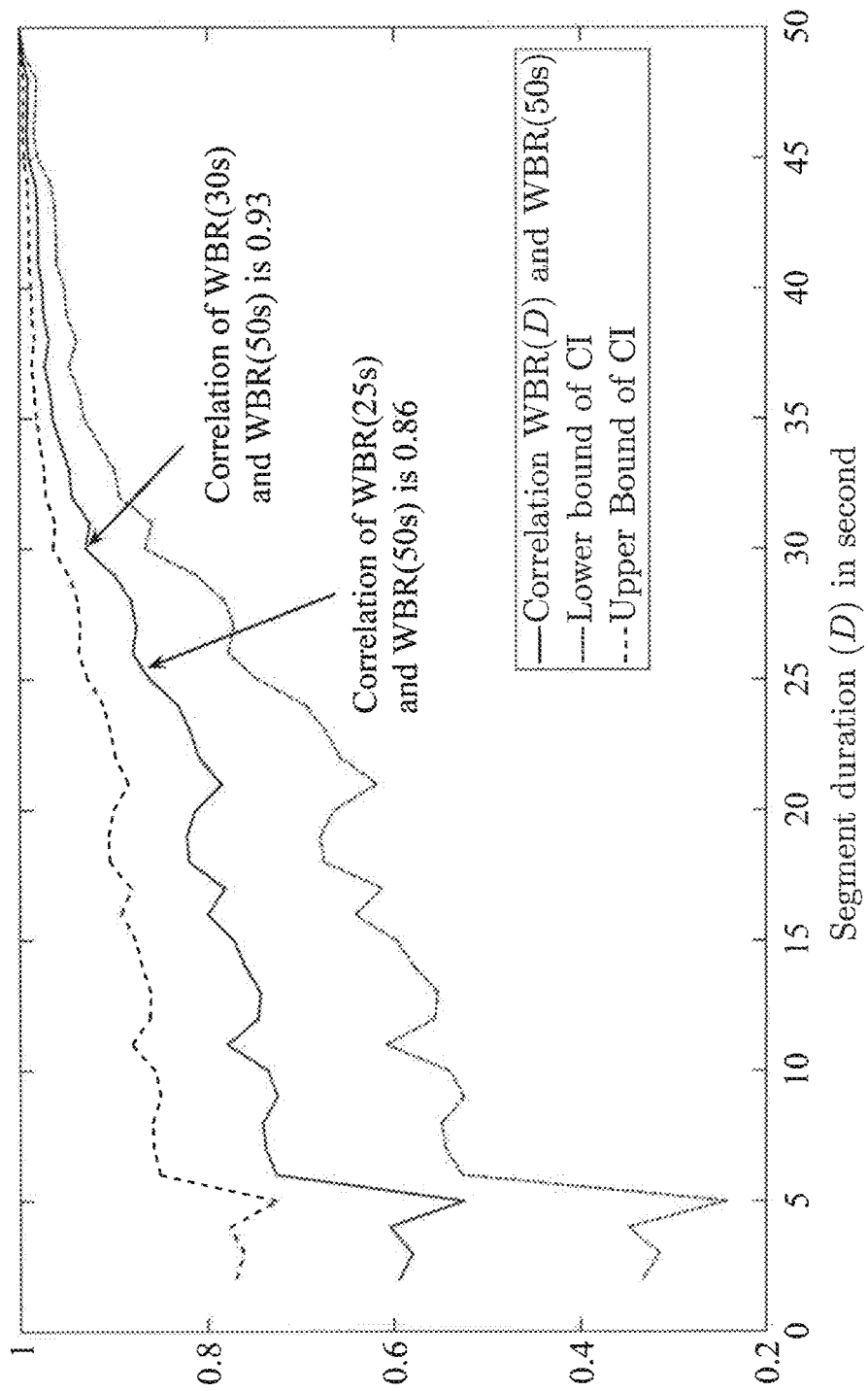

FIG. 5 is a plot showing the Pearson correlation between the wave break rate (WBR) obtained using a D-second segment and the one obtained from a 50 s segment, with 95% confidence interval (CI) bounds of the correlation.

Figures 6A, 6B, 6C:
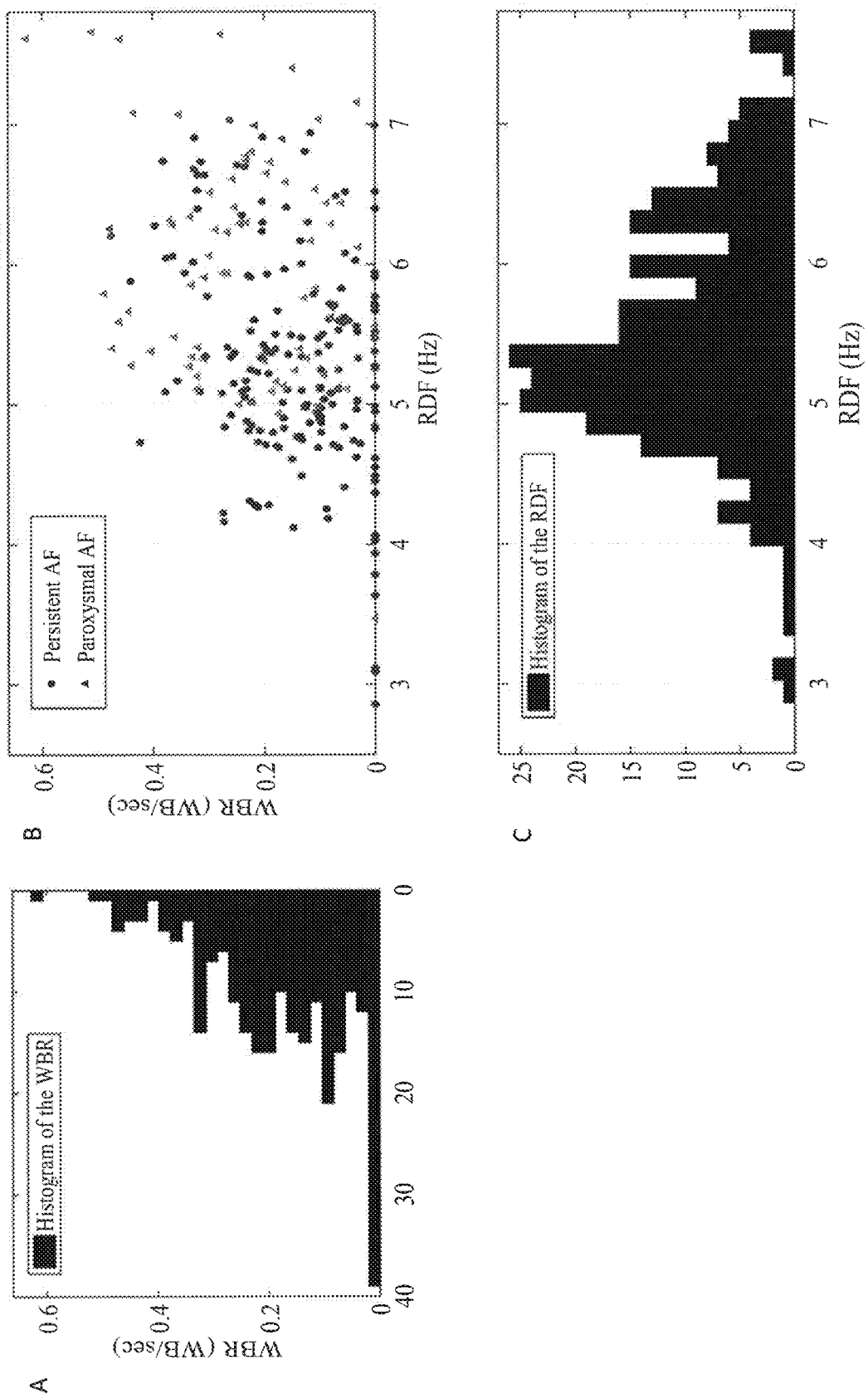

FIGS. 6A and 6C are histograms of wave break rate (WBR) in WB/sec and regional dominant frequency (RDF) in Hz, and FIG. 6B is a scatter plot of the WBR and RDF for 258 segments with durations longer than 25 s.

Figure 7A:
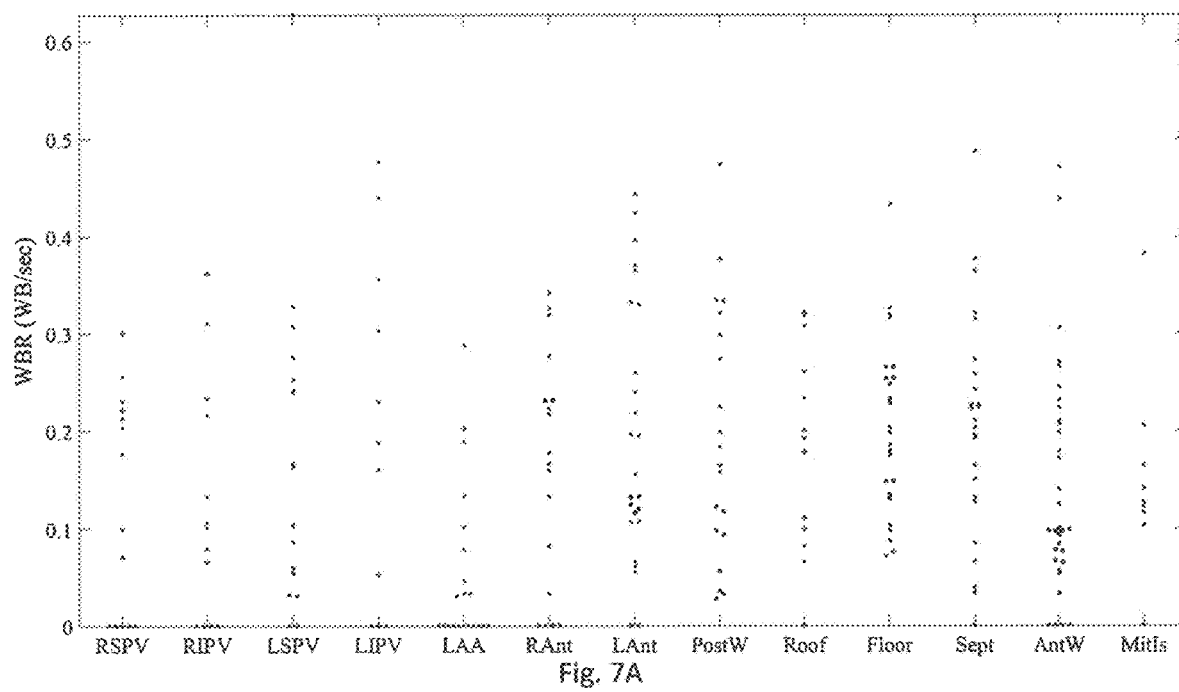
Figure 7B:
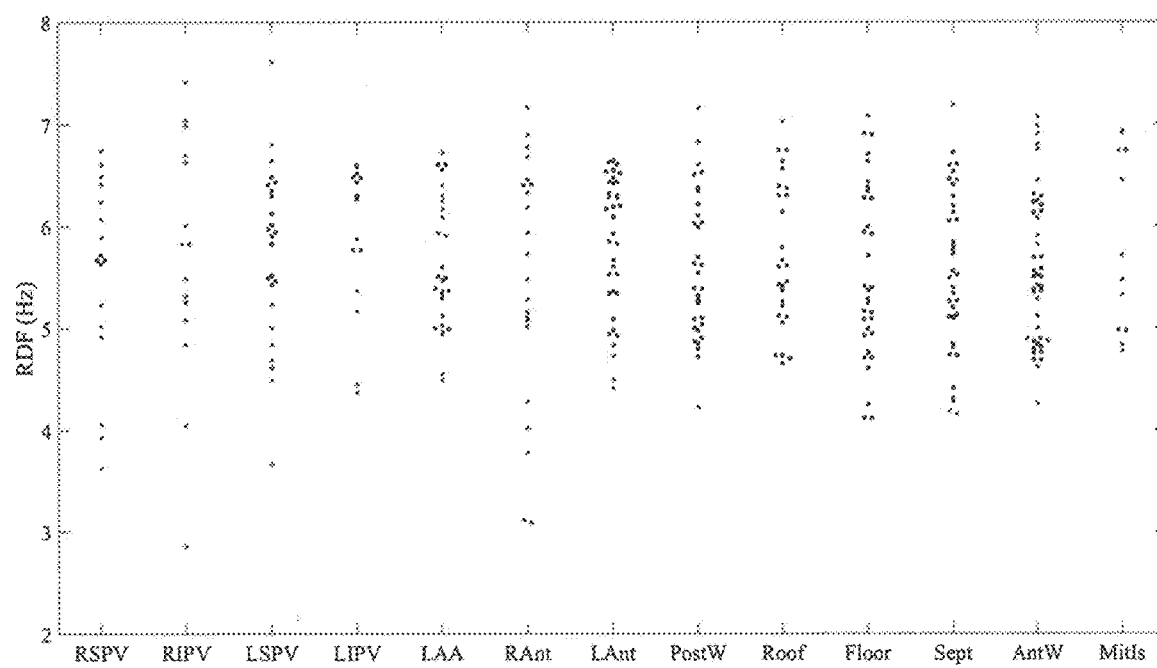

FIGS. 7A and 7B are plots showing estimated values for wave break rate (WBR) in WB/sec and regional dominant frequency (RDF) in Hz in different left atrial sites (RSPV: right superior pulmonary vein, RIPV: right inferior pulmonary vein, LSPV: left superior pulmonary vein, LIPV: left inferior pulmonary vein, LAA: left atrial appendage, RAnt: right antrum, LAnt: left antrum, PostW: posterior wall, Sept: septum, AntW: anterior wall, MitIs: mitral isthmus).

Figure 8:
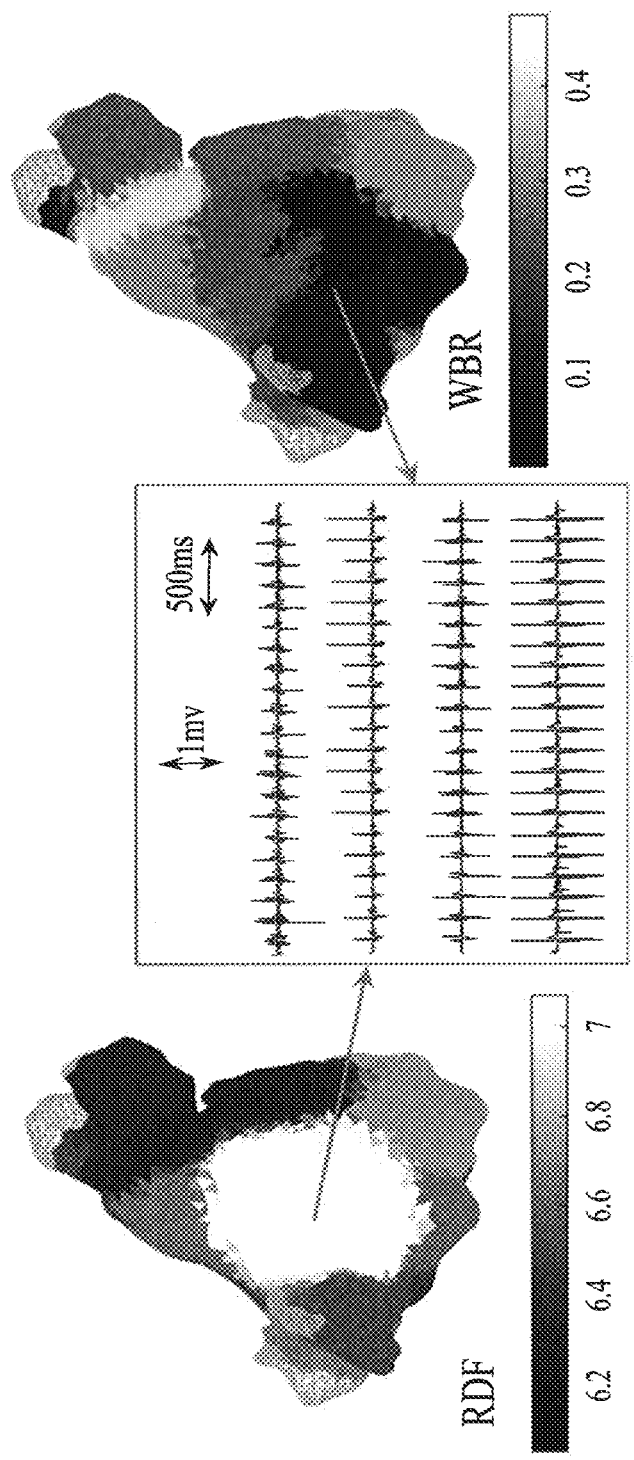

FIG. 8 shows two examples of three-dimensional atrial maps shaded based on the regional dominant frequency (RDF) and wave break rate (WBR); also shown is a plot of four bipolar IEGMs of the catheter at a site with high RDF (7 Hz) and low WBR.

Figure 9:
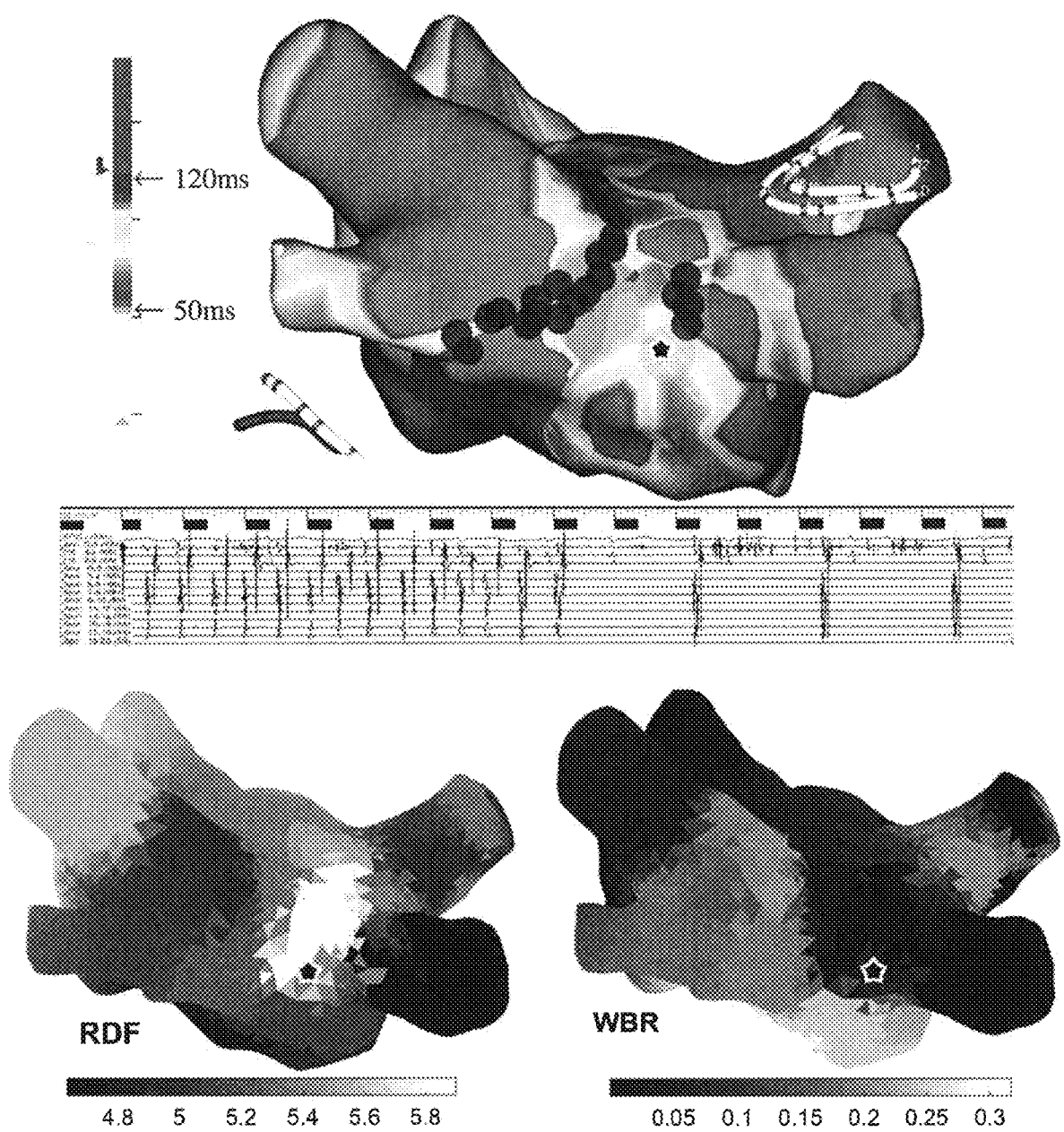

FIG. 9 (top) shows a 3D atrial map based on the mean complex fractionated electrogram (CFE) for a patient with persistent AF, wherein ablation sites are marked with filled circles; (middle) is a plot showing, from top to bottom, surface ECG (lead I), IEGMs of the ablation catheter placed at the location marked with star, IEGMs collected from catheters placed in coronary sinus (CS) and in the right superior pulmonary vein; (bottom) are atrial maps shaded based on the regional dominant frequency (RDF) and wave break rate (WBR) when 24 segments longer than 25 seconds were used to create these maps. In all the atrial maps, the ablation site that lead to AF termination is marked with star.

Figure 10A:
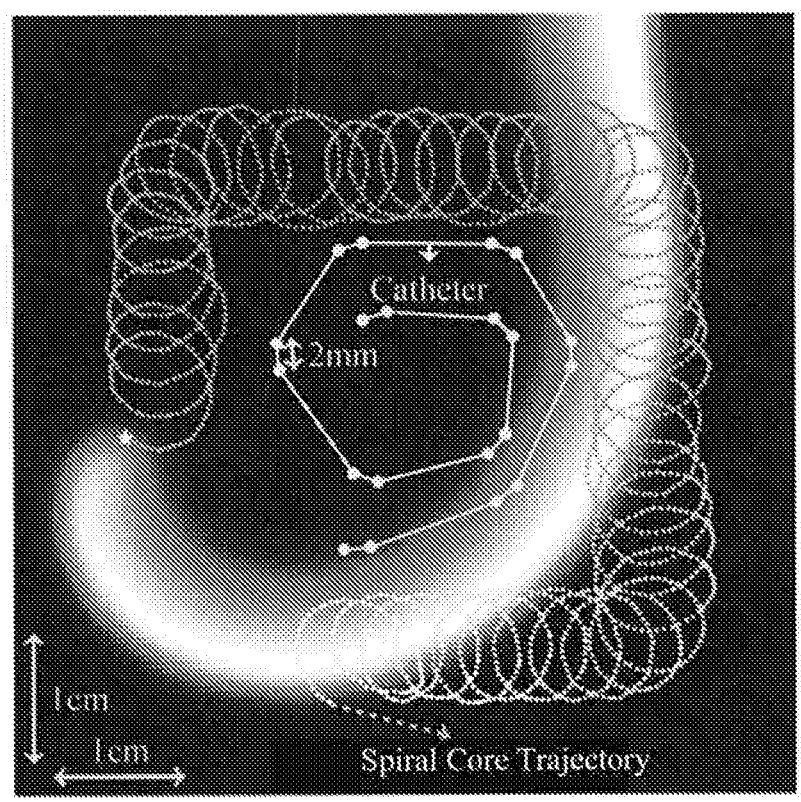
Figure 10B:
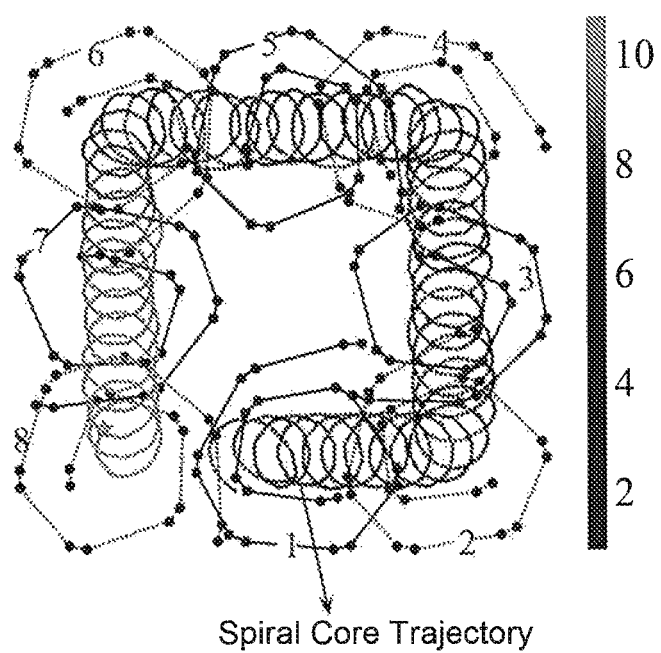
Figure 10C:
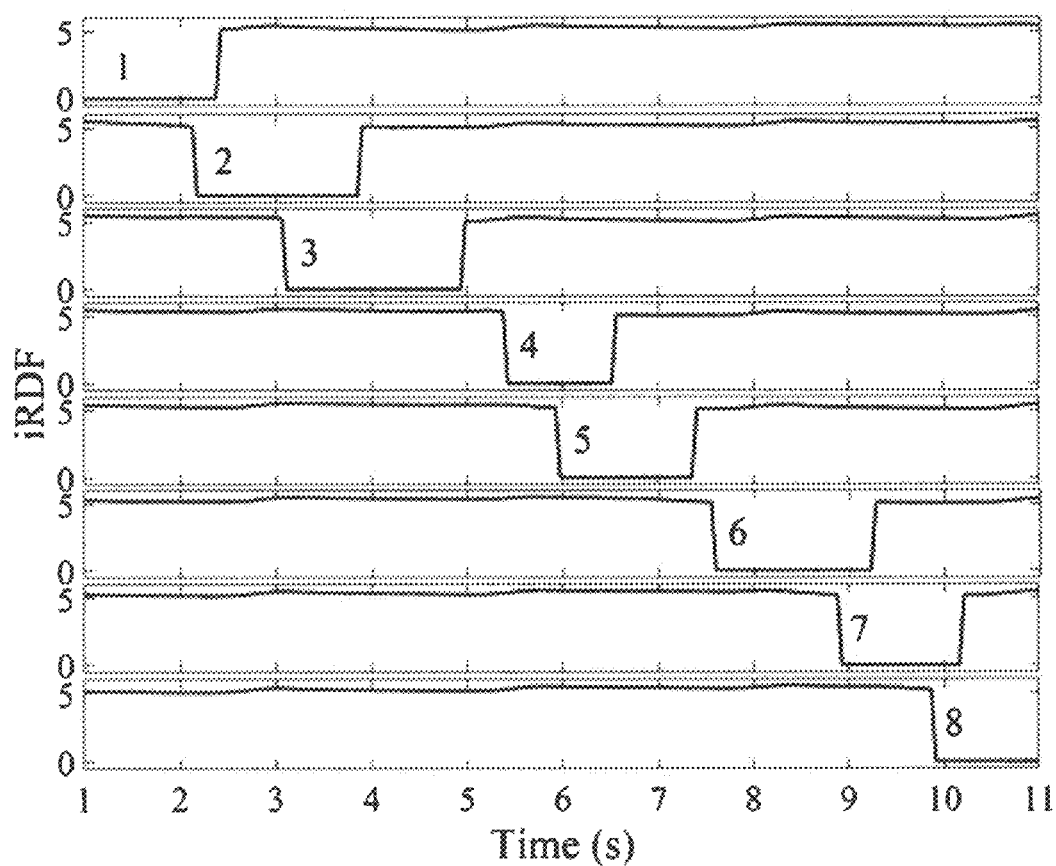

FIGS. 10A-10C show results of computer modelling, wherein FIG. 10A shows a spiral wavefront and a sample bipolar electrogram; FIG. 10B shows bipolar electrograms generated by placing the catheter in eight different sites (labelled 1 to 8); FIG. 10C shows the calculated iRDF of the catheter placements plotted as function of time (labelled 1 to 8).

Figure 11:
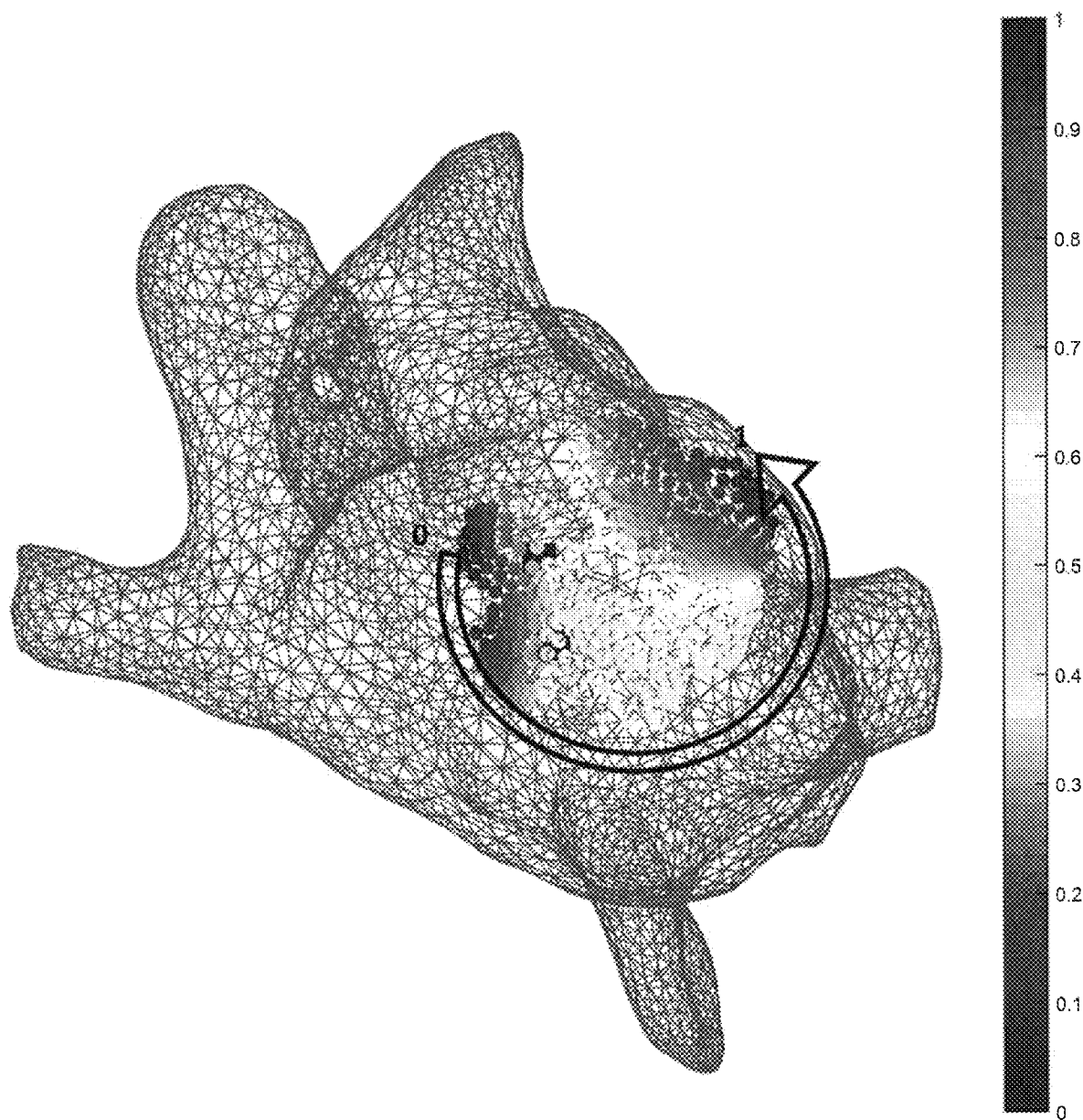

FIG. 11 is a propagation map showing local activation times of electrodes during the wave break observed at time 11 s in FIG. 2A, which were used to create an isochronal surface. The arrow shows the direction of rotational activities observed at this site.

DETAILED DESCRIPTION

Described herein are methods which consider the relationship between simultaneously recorded IEGM from electrodes and determine the wavefront characteristics of a region through time-frequency analysis of a regional feature. Relative delays between the activation times (ATs) of a mapping catheter's electrodes are time variant in AF, representing the dynamic melee of wavefronts as they pass the stationary catheter's position. As described herein, preprocessed IEGMs which are closely related to activation times are averaged to represent a regional feature. Frequency analysis of the resulting feature in a short time window is used to detect changes in wavefront dynamics for any sampled region. According to various aspects and embodiments of the invention, spatiotemporal heterogeneity in RDF and wavefront dynamics may be detected, characterized, and used to identify a region associated with the source of wave break during atrial fibrillation, which may be used to direct catheter ablation procedures, and/or used to evaluate catheter ablation outcomes in AF patients.

Figure 1A:
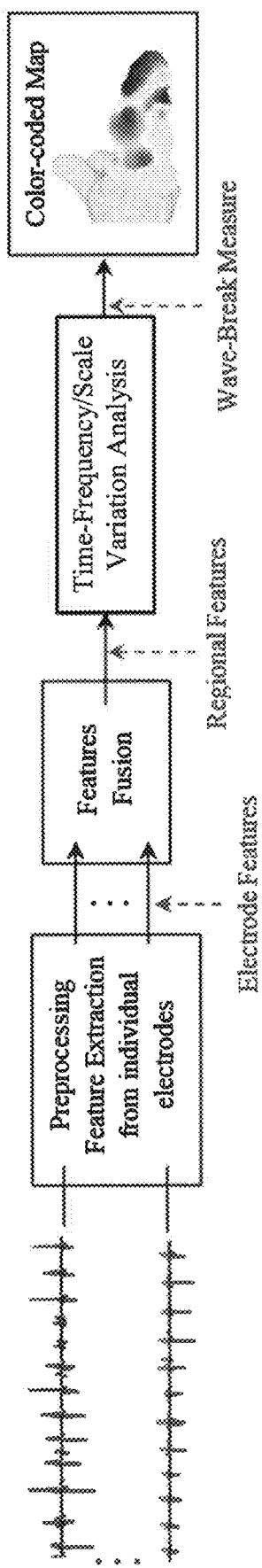
FIG. 1A is a block diagram showing a general framework for wave-break analysis as described herein.

A generalized framework is shown in the block diagram of FIG. 1A. Referring to FIG. 1A, in the first step features such as, but not limited to, electrogram active interval envelope, number of baseline occurrence (NO), instantaneous power, Shannon entropy, are extracted from intracardiac electrograms of individual electrodes. In the feature fusion block, the extracted features are combined (e.g., using weighted average) to extract regional features. Signal exclusion (e.g., exclusion of physiologically irrelevant signals, exclusion of electrodes with low signal to noise ratio and/or exclusion of an electrogram collected at a distance too far from the atrial surface (non-contact)) can be done in any of the first two steps. Time-frequency and/or time-scale analysis of the regional features is used to evaluate variations and irregularities in the wavefronts (i.e., wave-breaks). These results are then coded (e.g., by colour or other indicator) and shown e.g., graphically, such as on a three-dimensional (3D) map of the cardiac chamber.

An embodiment is described with respect to a study in which data were collected from twenty patients attending for diagnostic electrophysiologic studies with catheter ablation for AF. The study was approved by the institutional ethics committee of Queen's University at Kingston, Kingston, Ontario, Canada. Endocardial electrogram data were collected during sustained AF prior to ablation. For patients taking antiarrhythmic drugs (other than Amiodarone), the drugs were withheld five half-lives prior to the study. The left atrium was mapped using an electroanatomic mapping (EAM) system (EnSite™ Velocity™ system, St Jude Medical, MN) and a high definition mapping catheter, either a Reflexion™ HD or Spiral (St. Jude Medical). Each catheter has 20 electrodes; the bipolar pair electrodes spacing for Reflexion™ HD and Spiral are 2 mm and 1 mm, respectively. The data were collected at a sampling frequency of 2034.5 Hz. The EAM system was employed to ensure ample sampling and even coverage of the endocardial surface. In two patients recordings of one minute were obtained in order to establish a minimum duration required for robust experimental data (see section C and D, below). The data were recorded as segments and later exported to be used offline in the MATLAB™ (Mathworks, Natick, Mass.) environment for signal processing, as described below.

Locations of AF or atrial tachycardia (ATach) termination were labelled on the EAM during the procedure. The location of AF termination was compared with MATLAB generated maps and correlated subjectively. Procedural outcomes were reported as both immediate (termination of AF) and during follow up (recurrence of atrial arrhythmia).

1A. Regional Dominant Frequency and Wave Break Rate

The DF of each electrode of the catheter was extracted from the frequency analysis of the preprocessed IEGM of that electrode independent of the rest of the catheter's electrodes. To estimate the electrode DF (EDF), preprocessing was applied (e.g., [17]) to the IEGM recorded from each electrode, the mean amplitude of the resulting signal was removed, and the EDF was estimated from the extracted power spectrum. To obtain the power spectrum, short time Fourier transform (STFT) of the signal was calculated. For this, the signal was divided into segments with T second duration and 95% overlap. A Hanning window was applied on each segment and the power spectrum was estimated using the fast Fourier transform (FFT). Finally, the EDF of the ith electrode was calculated using $$EDF_i(t, T) = \underset{f}{\mathrm{argmax}}\, P_i(f, t, T) \qquad (1)$$

where $P_i(f, t, T)$ is the power spectrum obtained from ith electrode of the catheter.

Figure 1B:
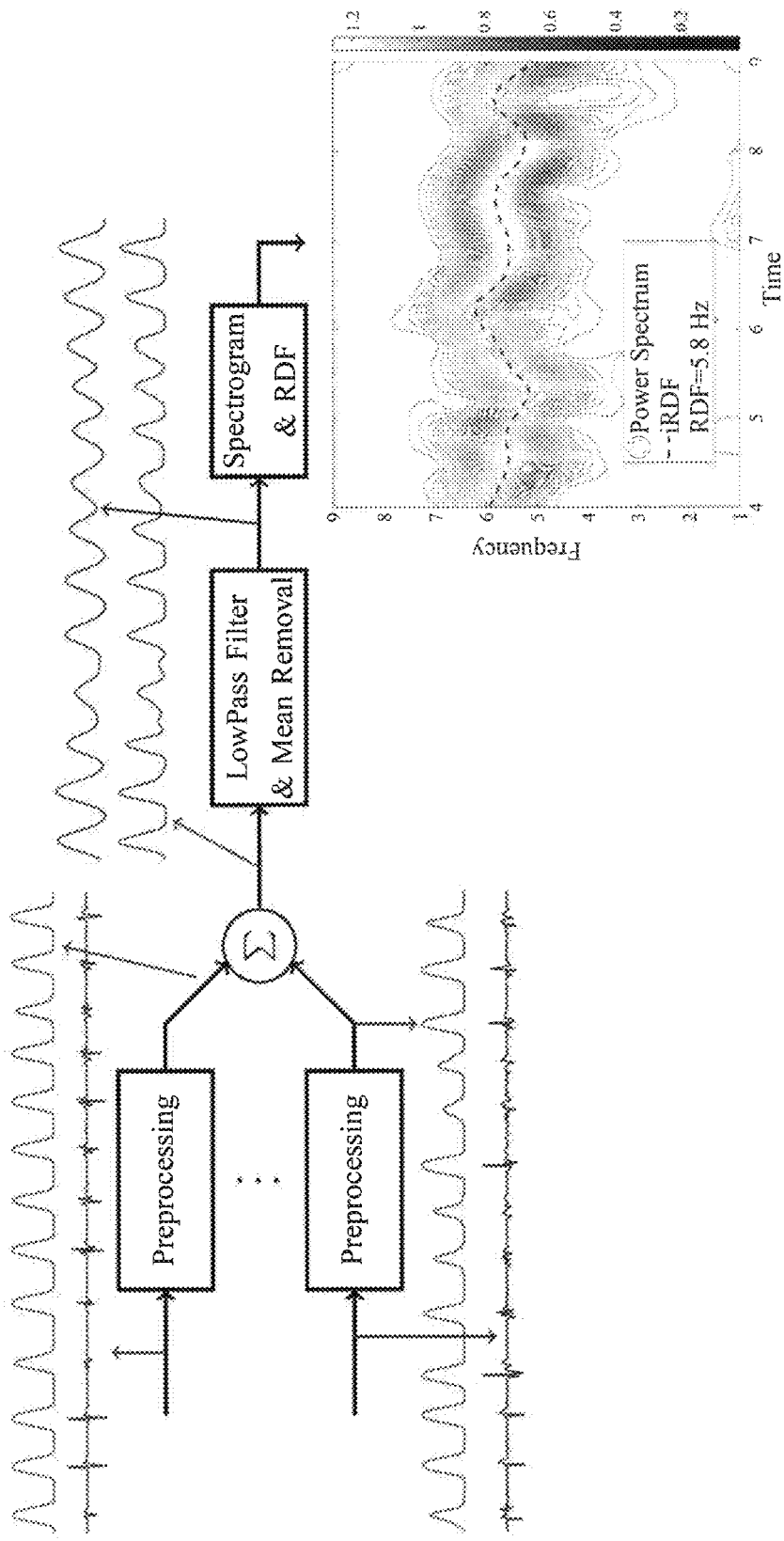
FIG. 1B is a block diagram showing method steps for regional dominant frequency (RDF) analysis and sample output at each step, according to one embodiment.

To obtain the regional DF (RDF), first, the IEGM of each electrode of the catheter was preprocessed to generate a smooth train of pulses on the active intervals of the electrogram. Then the preprocessed signals of all the catheter electrodes were averaged to produce one signal; this was smoothed by a low pass filter, and the mean amplitude was subtracted. Finally, the power spectrum of the resulting signal was used to estimate the DF, and the upper quartile extracted from the generated power spectrum was reported as the regional DF. FIG. 1B shows a flowchart of this embodiment, including sample output at each stage, as explained in more detail below.

Figure 1C:
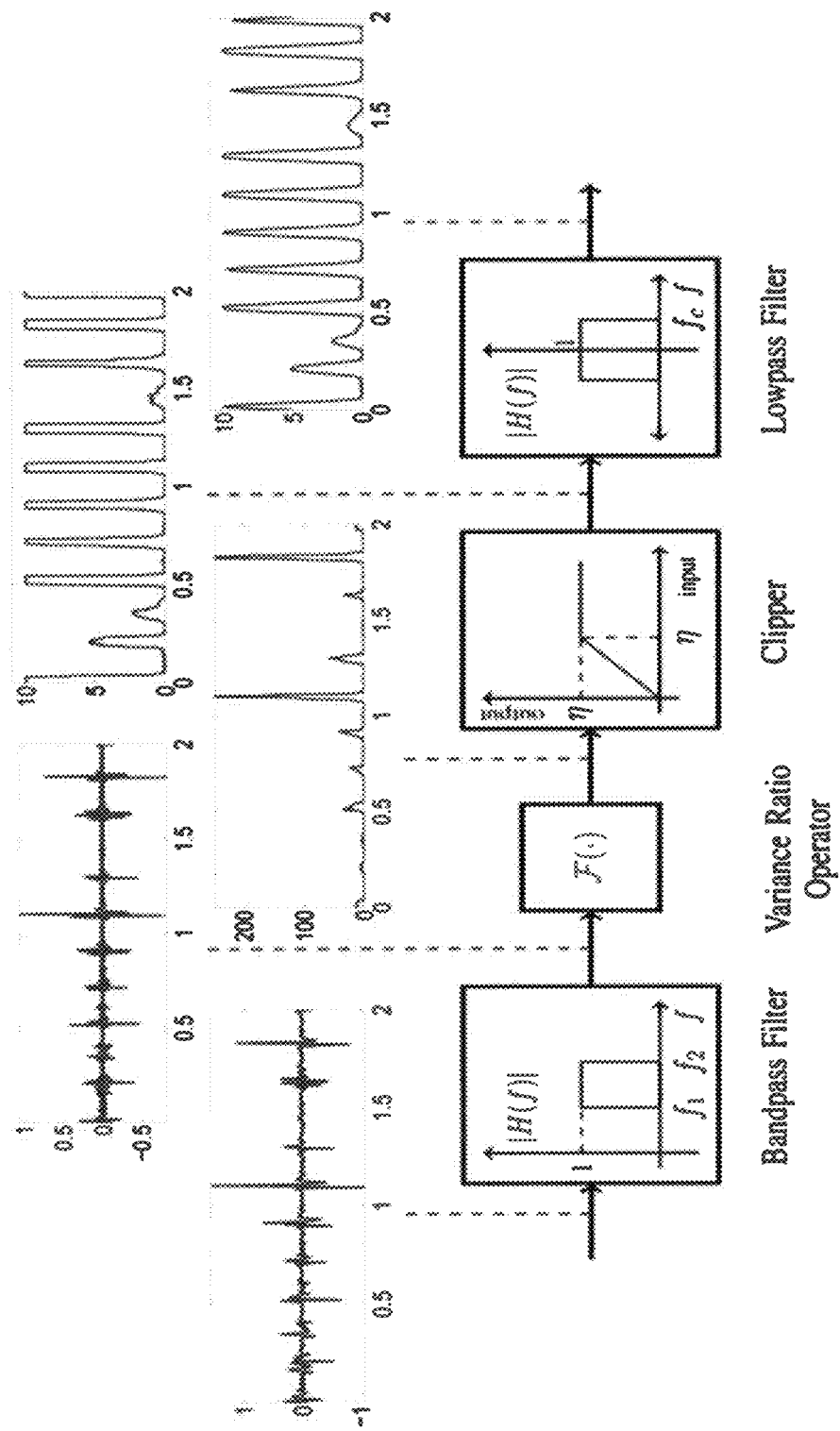
FIG. 1C is a block diagram showing a preprocessing block, and sample output at each step, according to one embodiment.

Similar to the EDF calculation, in the first stage of the RDF calculation, preprocessing was applied to the IEGM recorded from each electrode of the catheter. Preprocessing is used to replace the complex morphologies of the IEGMs with a smooth, simplified pulse shape, such as, for example, a Gaussian shape as shown in FIG. 1B. In one embodiment, a preprocessing step such as that in [17] may be used. FIG. 1C shows an example of a preprocessing block used to obtain regional dominant frequency, and shows sample output at each step. Preprocessing steps include a bandpass filter, a variance ratio operator [17], a clipper, and a lowpass filter. In one embodiment, values are $f_1$=40 Hz, $f_2$=250 Hz, $f_c$=20 Hz, and $\eta$=10.

The AT of each bipolar electrode may be obtained by threshold crossing the associated preprocessed signal. However, here, the processed signal is used as an indicator of IEGM active intervals without trying to extract local ATs of electrodes which are prone to error. The preprocessed signals of all the electrodes were then averaged. The following two-sided exponential finite impulse response (FIR) filter (h) with a length of L was then used to further smooth the processed signal and allow estimation of discontinuities in the wavefront propagation or WB:

$$h'_n = \exp\left(-\left|-1 + \frac{2(n-1)}{L}\right|\right), \qquad (2)$$

$$h_n = \frac{h'_n}{\sum_{k=1}^{L} h'_k}, \text{ for } n = 1, \ldots, L.$$

For example, L=220 was used for the cases reported herein. This value or filter type may of course be adjusted according to the sampling rate, DF, or mean cycle lengths of atrial activations.

The mean amplitude of the resulting signal was removed and, in the next stage, the STFT of the signal was calculated in a similar manner to the EDF to obtain its power spectrum, i.e., the signal was divided into segments with T second duration and 95% overlap, the Hanning window (other windows such as, but not limited to, Rectangular, Triangular, Hamming, Gaussian, Blackman, etc., may be used) was applied on each segment, and the power spectrum of the signal was estimated using the FFT. The instantaneous RDF (iRDF) and upper quartile of iRDF, (denoted as RDF) were calculated from the extracted power spectrum, i.e., $$iRDF(t, T) = \mathrm{argmax}_f P(f, t, T) \qquad (3)$$

$$RDF(D, T) = \mathrm{upper\ quartile}_{t \in [0,D]} iRDF(t, T) \qquad (4)$$

where T is the duration of the segments used in the STFT, D is the duration of the IEGM segment, and P(f, t, T) is the power spectrum of the output of the 2-sided exponential lowpass filter which depends on time, frequency and T.

The time window T in the STFT was selected to be a small value, to increase time resolution of the extracted iRDF and enable identification of WB. In this example, T was selected to be equal to one second. However, other values of T may be used, such as, but not limited to, 0.5-3.0 s. For example, T may be two seconds. Such values are smaller than that commonly used for EDF calculations (see, e.g., [16,18]). Increasing T beyond these values increases the frequency resolution and degrades the time resolution, thus obscuring transient WB events. WB is defined herein as any drop in the iRDF which is more than 3 Hz below the RDF (or below 0.5 Hz) and lasts longer than 100 m. Finally, the number of WBs per second (i.e., wave break rate (WBR)) was used as a feature/measure to characterize (e.g., quantify, assess quality) of the wavefront propagation at each site. Specific values used herein are user-defined thresholds and the invention is not limited thereto.

1B. Example of RDF-Based Wave Break Identification

In FIG. 2A the top ten plots are IEGMs recorded from electrodes of a Reflexion™ Spiral catheter from the roof of the left atrium of a patient with persistent AF. The outputs of various stages of processing are also plotted for this segment. For the regions where a clear wavefront is present, the peaks of the preprocessed signals of all the electrodes occur very close to each other, therefore, the averaged signal generates a large peak for each wavefront (see FIG. 2B). However, for the areas/time intervals where a WB occurs, e.g., due to slow conduction velocity, the delays between the ATs of the electrodes increase and, consequently, the peaks of the preprocessed signals occur during a longer time interval. In this case, averaging the preprocessed signals generates several small peaks resulting in a segment with high frequency. This high frequency component of the signal was attenuated significantly by the two-sided exponential low pass filter leading to a drop in the iRDF (see FIG. 2C). This example shows how changes in iRDF can be used to study the wavefront variation and identify WBs. As shown in the bottom plot of FIG. 2A, three WBs are present in this IEGM segment (at around time=12, 14, and 24 s), and the WBR for this segment is estimated to be 0.1 WB/sec.

1C. Minimum Required Segment Duration for Accurate RDF Estimation

Here, the aim was to find the minimum segment duration that is required for an accurate and robust estimation of the RDF. It was assumed that the feature obtained using the 30-second segment was accurate and robust (i.e., the "gold standard"), e.g., RDF (D=30 s, T=1 s) is an accurate estimate of the segment RDF. The goal was to find the segment duration such that the Pearson correlation between the desired feature obtained from that segment and the gold standard is higher than 85%. IEGMs of the patients with durations longer than 30 seconds were selected (201 segments were selected from 15 patients) and the RDF (30 s, 1 s) was calculated for them. The RDF was also calculated using shorter segment durations D and the results compared. FIG. 4 shows the Pearson correlation between the RDF (D, 1 s) and the RDF (30 s, 1 s) for various Ds, with the upper and lower bounds of the confidence interval (CI) of the correlation are also plotted. From this figure, it was concluded that the RDF obtained using an IEGM segment longer than four seconds is an accurate estimate of the RDF (30 s, 1 s), as the correlation of the RDF (4 s, 1 s) and RDF (30 s, 1 s) is 90%.

1D. Minimum Required Segment Duration for Accurate WBR Estimation

Having established that the use of four second segments provides accurate estimation of the RDF, the objective in this section was to find the minimum required segment duration for reliable WBR estimation. It was expected that much longer segment duration would be required for WBR estimation. Thus, the same procedure as in the previous section was followed. Segments with duration D longer than 50 s (37 segments) were selected from two patients, and for each segment, the WBR was obtained using the first 50 seconds of each segment. The Pearson correlation (and the 95% CI bounds) of the WBRs estimated from D-second segments and 50-second segments are plotted in FIG. 5. Based on this figure, it was concluded that IEGM segments longer than 25 s are required for reliable estimation of the WBRs.

1E. Statistics

The Anderson-Darling test was used to inspect for normality. Nonparametric data was compared using the Mann-Whitney test and was used to compare the WBR and RDF of persistent and paroxysmal patients; and Spearman's rank correlation coefficient used to study the correlation between WB and RDF. (a p value less than 0.05 is considered statistically significant). The mean and standard deviation of variables are reported using the mean±std notation.

1F. Implementation

Embodiments may be implemented at least partially in software (e.g., an algorithm). The software may include programmed media for use with a processor (e.g., a computer) and with data such as, for example, IEGM data from electrodes, the programmed media comprising a computer program stored on non-transitory storage media compatible with the computer, the computer program containing instructions to direct the processor to perform one or more of the functions described above and/or in FIG. 1.

The computer may include a data processing system that controls one or more components of the system, in conjunction with a user interface (e.g., a graphical user interface (GUI)). Controlling may include functions such as receiving input (e.g., IEGM data), analyzing data, and displaying results and/or images on a display of the system. The data processing system may be a client and/or server in a client/server system. For example, the data processing system may be a server system or a personal computer (PC) or tablet-based system. The data processing system may include an input device, a central processing unit (CPU), memory, display device, and interface device. The input device may include a keyboard, a mouse, a trackball, a touch sensitive surface or screen, or a similar device. The display may include a computer screen, television screen, display screen, terminal device, a touch sensitive display surface or screen, or a hardcopy producing output device such as a printer or plotter. The memory may include a variety of storage devices including internal memory and external mass storage typically arranged in a hierarchy of storage as understood by those skilled in the art. For example, the memory may include databases, random access memory (RAM), read-only memory (ROM), flash memory, and/or disk devices. The interface device may include one or more network connections. The data processing system may be adapted for communicating with other data processing systems over a network via the interface device. For example, the interface device may include an interface to a network such as the Internet and/or another wired or wireless network (e.g., a wireless local area network (WLAN), a cellular telephone network, etc.). Thus, the data processing system may be linked to other data processing systems by the network. The CPU may include or be operatively coupled to dedicated coprocessors, memory devices, or other hardware modules. The CPU is operatively coupled to the memory which stores an operating system for general management of the system. The CPU is operatively coupled to the input device for receiving user commands or queries and for displaying the results of these commands or queries to the user on the display. Commands and queries may also be received via the interface device and results may be transmitted via the interface device. The data processing system may include a database system (or storage) for storing data and programming information. The database system may include a database management system and a database and may be stored in the memory of the data processing system. In general, the data processing system has stored therein data representing sequences of instructions which when executed cause certain steps of the method described herein to be performed. For example, the instructions may be associated with one or more components of FIG. 1. Of course, the data processing system may contain additional software and hardware, a description of which is not necessary for understanding the invention.

Thus, the data processing system includes computer executable programmed instructions for directing the system to implement the embodiments of the invention. Executing instructions may include the system prompting the user for input at various steps, some of which are shown in the embodiments of FIG. 1. In one embodiment the programmed instructions may be embodied in one or more hardware modules or software modules resident in the memory of the data processing system or elsewhere. In one embodiment the programmed instructions may be embodied on a non-transitory computer readable storage medium or product (e.g., a compact disk (CD), etc.) which may be used for transporting the programmed instructions to the memory of the data processing system and/or for executing the programmed instructions. In one embodiment the programmed instructions may be embedded in a computer-readable signal or signal-bearing medium (or product) that is uploaded to a network by a vendor or supplier of the programmed instructions, and this signal or signal-bearing medium may be downloaded through an interface to the data processing system from the network by end users or potential buyers.

A user may interact with the data processing system and its hardware and software modules using a GUI. The GUI may be used for controlling, monitoring, managing, and accessing the data processing system. GUIs are supported by common operating systems and provide a display format which enables a user to choose commands, execute application programs, manage computer files, and perform other functions by selecting pictorial representations known as icons, or items from a menu through use of an input device such as a mouse or touch screen. In general, a GUI is used to convey information to and receive commands from users and generally includes a variety of GUI objects or controls, including icons, toolbars, drop-down menus, text, dialog boxes, buttons, and the like. A user typically interacts with a GUI presented on a display by using an input device (e.g., a mouse or touchscreen) to position a pointer or cursor over an object (e.g., an icon) and by "clicking" on the object. Typically, a GUI based system presents application, system status, and other information to the user in one or more "windows" appearing on the display. A window is a more or less rectangular area within the display in which a user may view an application or a document. Such a window may be open, closed, displayed full screen, reduced to an icon, increased or reduced in size, or moved to different areas of the display. Multiple windows may be displayed simultaneously, such as: windows included within other windows, windows overlapping other windows, or windows tiled within the display area.

1G. Results

Five patients from 20 were excluded due to poor data quality and incomplete coverage of the left atrial chamber defined as endocardial surface coverage of less than 60%. Average procedural duration for the remaining 15 patients was 4:39±0:54 hours (persistent 4:53±0:42 hours, paroxysmal 4:12±1:09 hours). There were 13 males; mean age 61.3±9.2 years; 5 paroxysmal AF; 10 persistent AF (mean duration of persistent AF 20.6±8.6 months); the mean left atrial diameter was 47±9.4 millimeters (persistent 50.9±7.8 millimeters and paroxysmal 39.2±7.7 millimeters). There was an average of 24.4±7 recording locations per patient and mean recording duration of 29.9±9.8 seconds. In 8/10 persistent patients Ibutilide 1 mg was administered prior to sampling of the AF electrograms.

Segments longer than 25 s were selected from 15 patients (279 segments). The first 25 s of each segment was used for the RDF and, consequently, the WBR estimation. The mean RDF of the segments was 5.5±0.82 Hz (median 5.4 Hz; range, 2.86 to 7.66 Hz), and the WBR was 0.16±0.13 WB/sec (median 0.15 WB/sec; rang, 0 to 0.63 WB/sec). The RDF and WBR for the five paroxysmal patients was 5.99±0.8 Hz (median 5.94; range, 3.47 to 7.66 Hz) and 0.24±0.14 (median 0.23; range, 0 to 0.63 WB/sec) respectively. For the ten persistent patients, the RDF and WBR was 5.32±0.75 Hz (median 5.27; range, 2.86 to 7.03 Hz) and 0.14±0.11 (median 0.13; range, 0 to 0.47) respectively. The difference was significant ($p<0.001$) for both RDF and WBR.

There was significant heterogeneity in distribution of WB and RDF, as the two measures were weakly correlated (0.3; $p<0.001$). FIG. 6B shows a scatter plot of the estimated WBR and RDF, in which circles and triangles are used to mark the estimated values from the patients with persistent and paroxysmal AF, respectively. The histograms of the WBR (in WB/sec) and RDF (in Hz) are also shown in FIGS.

6A and 6C, respectively. FIGS. 7A and 7B show the estimated values for the WBR and RDF, respectively, at different left atrial sites for all the segments collected from the patient cohort. There was a trend toward relatively low WBR in the left atrial appendage and both the anterior wall and veins, but overall there was non-significant variation in relative values across the LA geometries.

Of the 15 patients, ablation terminated AF to sinus rhythm in six patients and ATach in three; a further six patients underwent direct current cardioversion at the discretion of the operator. Sites where termination of AF occurred with ablation were plotted with the geometries populated with RDF and WBR data. Sites of high RDF and low WBR (↑RDF,↓WBR) were defined as sites where RDF and WBR were in the upper and lower quartile range of the calculated values for each patient, respectively. Thus, a ↑RDF,↓WBR site was described based on the relative values in each patient and not absolute values; these sites were identified in scale) for CFEmean; the area just posterior to the RIPV is observed to present high RDF and low WBR with an area immediately inferior showing a high WBR. In FIG. 9, the top panel shows a 3D atrial map based on the mean complex fractionated electrogram (CFE) for a patient with persistent AF, wherein ablation sites are marked with dots; the middle panel is a plot showing, from top to bottom, surface ECG (lead I), IEGMs of the Cool Flex™ (St. Jude Medical) ablation catheter placed at the location marked with star, IEGMs collected from the Inquiry™ (St. Jude Medical) catheter placed in coronary sinus (CS), and from Reflexion™ Spiral (St. Jude Medical) placed in right superior pulmonary vein; and at the bottom are atrial maps shaded based on the regional dominant frequency (RDF) and wave break rate (WBR) when 24 segments longer than 25 seconds were used to create these maps. In all the atrial maps, the ablation site that lead to AF termination is marked with star.

TABLE 1

Patient demographic data, procedural data, and outcome. Value 0 in 'persistent AF duration' column represents paroxysmal patient. (AF: atrial fibrillation; LA: left atrium; M: male; F: female; CV: cardioversion; SR: sinus rhythm; ATach: atrial tachycardia; NA: not applicable)

| Gender | Age | Persistent AF Duration (months) | LA diameter (millimeter) | Number of ↑RDF-↓WBR | All ↑RDF-↓WBR Ablated | Outcome of procedure | ↑RDF-↓WBR site of termination | Recurrence |
|---|---|---|---|---|---|---|---|---|
| M | 62 | 0 | 34 | 4 | 1 | CV to SR | NA | 0 |
| M | 77 | 24 | 57 | 3 | 0 | CV to SR | NA | AF |
| M | 60 | 10 | 55 | 4 | 0 | CV to SR | NA | 0 |
| M | 80 | 18 | 47 | 3 | 0 | CV to SR | NA | AF |
| M | 67 | 28 | 54 | 1 | 1 | CV to SR | NA | ATach |
| M | 49 | 18 | 52 | 4 | 0 | CV to SR | NA | ATach |
| M | 60 | 0 | 31 | 3 | 1 | ATach | 1 | 0 |
| M | 54 | 24 | 52 | 2 | 1 | ATach | 1 | 0 |
| M | 56 | 36 | 65 | 2 | 1 | ATach | 1 | ATach |
| M | 49 | 6 | 38 | 1 | 1 | SR | 1 | 0 |
| F | 59 | 0 | 39 | 0 | NA | SR | NA | 0 |
| M | 65 | 0 | 51 | 2 | 1 | SR | 0 | 0 |
| M | 60 | 18 | 41 | 3 | 1 | SR | 0 | 0 |
| F | 69 | 24 | 48 | 1 | 1 | SR | 1 | 0 |
| M | 52 | 0 | 41 | 2 | 1 | SR | 1 | 0 |

14/15 patients (2.6±1.2 sites per patients; range, 1 to 4 sites; 43% situated within the pulmonary veins). FIGS. 8 and 9 are illustrative. In FIG. 8 the roof of the left atrium shows very high frequency with very low WBR observed on the sampled electrograms. This area terminated AF during a wide area circumferential ablation prior to isolation of the right sided veins.

Nine patients had termination of AF with ablation. In 5/6 patients where AF terminated to sinus rhythm ↑RDF,↓WBR sites were present and ablated, in 3/3 patients where AF terminated to ATach, ↑RDF,↓WBR sites were present and ablated, and in 6/9 patients ↑RDF,↓WBR sites were located at sites of termination. In one patient no ↑RDF,↓WBR site was observed; this patient had a history of paroxysmal AF and terminated to sinus rhythm during right pulmonary vein antral ablation.

Of the six patients that underwent cardioversion, only two had sites with ↑RDF,↓WBR ablated. During follow up of those patients, four had recurrence (ATach (two) and AF (two)). No recurrence was reported in the cohort of six patients that ablation successfully terminated AF to sinus rhythm, whereas among three patients that terminated to ATach, one had ATach recurrence. Table 1 summarizes these results.

FIG. 9 highlights an ablation that terminated the AF to sinus rhythm on a geometry colour coded (shown in gray- 1H. Discussion The methods described herein provide a novel metric for further investigation, mapping, and understanding of AF that overcomes the drawbacks of traditional electrogram and anatomical-guided ablation (pulmonary vain isolation, lines, CFE, EDF) treatment for persistent AF [15,19]. Regional dominant frequency identifies regions with rapid change in wavefront propagation. This is done without directly identifying the activation time at individual bipoles, as accurate local activation time estimation is very challenging [5]. The methods are more robust and efficient than traditional methods and can be used to identify and characterize wavefronts with long/fractionated/non-discrete activations and without clear isoelectric lines between activations. The methods are robust against the unorganized activations during WBs that result from rotating waves, local conduction block, and wavefront collision such that WB characteristics may be quantified at each atrial site to provide information about AF mechanism and perpetuation. The methods provide a computationally efficient algorithm to identify and quantify regional wavefront discontinuities or WBs for further characterization of AF patterns. These were examined in the context of acute procedural outcomes and showed an association between termination sites and wavefront dynamics. It was observed that sites with high RDF and low WBR (↑RDF, ↓WBR) are associated with termination of AF; this is in keeping with experimental data on sources [21,22]. Moreover, it is expected that the technique will be able to differentiate regions with high frequencies resulting from colliding wavefronts, from anchored, stable AF drivers by combining the RDF and WBR metrics.

The study of the spatial distribution of WBR and RDF might provide clinically important insight regarding putative sources of AF as suggested in these early data. The WBR is proposed as a feature/measure to quantify the quality of the wavefront propagation at each site; it can be shown on electroanatomic mapping systems and employed to characterize and differentiate signal complexity leading to the potential for a more informed choice of ablation target than current empiric techniques. Importantly, the data is collected sequentially but used regionally, which provides improved endocardial resolution over panoramic surface ECG and current balloon-based technologies. As shown herein, four seconds is sufficient for RDF reproducibility at any site and the addition of WBR can be performed within 25 seconds of data collection. These early data suggest that an expedited protocol that examines only WBR rate at high DF sites to differentiate putative source from collision may be feasible. It is expected that regional features such as wave break duration percentage require segments with shorter duration, which suggests that this method may be used during ventricular fibrillation.

WB was quantified at each site by estimating the WBR which describes the number of WBs per second. Other measures for quantifying WB include longest WB duration throughout the recording time, average or shortest time between consecutive WBs, or WB duration percentage defined as the total WB duration divided by IEGM segment duration.

Furthermore, recording sites with (↑RDF, ↓WBR) were described as critical sites. Other possibilities for critical sites may be sites with high WBR and low amplitude or sites with WBR higher than user-defined threshold.

Here, ↑RDF,↓WBR site was described based on the relative values in each patient. Evaluation of absolute values may also be done by using user-defined thresholds for the measured features.

According to the exemplary study described herein, accurate estimation of the WBR requires 25 s stable positioning at each recording site. For the 15 patients the mean time for electrogram collection for the left atrium alone was 27±8 min. However, it is expected that this time can be reduced with WBR focusing only on high RDF sites identified through four second segments. In addition, if a goal is to localize sites with high WB measures (e.g., high WBR sites), long recordings are not needed and shorter segments can be used to identify those sites.

Ibutilide was used in 8/10 persistent patients and none of the five paroxysmal patients. The use of Ibutilide to facilitate catheter ablation is still debated; however, the potent class III effect will reduce mean AF cycle length and consequently RDF values [23]. This may explain why the mean RDF for paroxysmal patients was significantly higher than for persistent patients, contrary to the available literature [8].

Stability of the generated map throughout procedure duration is a critical factor, as any shift and drift in the initial map limits the ability to accurately associate WBR or RDF to their recording sites during the ablation portion of the procedure. Although care was taken in the mapping, significant change was observed in geometry location and instability that required correction that necessitated subjective correlation between ablation sites and ↑RDF, ↓WBR sites.

Furthermore, electrograms were collected exclusively from the left atrium and the right atrium during AF is not represented in the analysis.

2. Computer Modelling of Spiral Rotor and Associated Wave Break Analysis

In this section, a computer model was used to simulate the electrical activities of cardiac cells. More specifically, the simulation included a spiral rotor with meandering core which sustained the cardiac electrical activities. The simulated electrograms were used to estimate the iRDF and identify WBs. The results showed that the iRDF-drop or WB happens when the core of simulated rotor wavefront passes the area under the catheter.

To generate a rotor a modified FitzHugh-Nagumo model was used with membrane parameters described in Table I of [1]. The spiral wavefront was generated by cross-field stimulation method (homogeneous and isotropic array) [2]. A two-dimensional partial differential equation with Neumann no-flux boundary conditions was numerically solved by the finite difference method, and the diffusion terms were calculated using a five-point formula. Ghost points were deployed to include the Neumann boundary conditions [3], and the Euler method of integration were implemented to solve the differential equations [2]. Unipolar electrograms were calculated with sampling frequency of 1000 sample/second, using current source approximation for a large volume conductor [4], and consequently, the bipolar electrograms were obtained from unipolar electrograms.

FIG. 10A shows the simulated spiral wavefront and its core trajectory, wherein the meandering core is marked with a star and its trajectory is colour-coded (shown in grayscale) based on time. A sample catheter with 20 electrodes and a bipolar pair electrode spacing of 2 mm is also shown. The bipolar electrograms generated from placing the catheter in eight different sites, labelled 1-8, (FIG. 10B) were processed to calculate iRDF; these iRDF are plotted in FIG. 10C as a function of time. This figure shows that there is a significant drop in iRDF (or WB) when the core of rotor passes the area under the catheter (no WB was observed in the collected electrograms of the catheter shown in FIG. 10A. This simulation showed that sites which are more frequently in a rotor core travelling path experience more WBs and consequently would be highlighted in the WBR map as good candidates for ablation.

3. Clinical Example of an Identified Rotor During Wave Break

FIG. 11 shows an example of rotational activity observed during wave break. Local activation times of electrodes may be used to create a propagation map, and the atrial surface may be colour coded to illustrate the isochronal surfaces. FIG. 11 is a propagation map created using the activation times of electrograms plotted in FIG. 2A during wave break at time 11 s. The arrow shows the direction of rotational activities observed at this site, beginning at 0 and ending at 1. Although shown in greyscale, the dots on the map may be colour-coded according to the scale on the right, from, e.g., blue at 0, through green at 0.5, to red at 1.

The contents of all cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] J. M. Rogers and A. D. McCulloch, "A collocation-galerkin finite element model of cardiac action potential propagation," IEEE Transactions on Biomedical Engineering, vol. 41, no. 8, pp. 743-757, 1994.

[2] A. M. Pertsov, J. M. Davidenko, R. Salomonsz, W. T. Baxter, and J. Jalife, "Spiral waves of excitation underlie reentrant activity in isolated cardiac muscle." Circulation research, vol. 72, no. 3, pp. 631-650, 1993.

[3] J. W. Thomas, Numerical partial differential equations: finite difference methods. Springer Science & Business Media, 2013, vol. 22.

[4] V. Jacquemet, N. Virag, Z. Ihara, L. Dang, O. Blanc, S. Zozor, J. Vesin, L. Kappenberger, and C. Henriquez, "Study of unipolar electrogram morphology in a computer model of atrial fibrillation," Journal of cardiovascular electrophysiology, vol. 14, no. s10, 2003.

[5] M. H. Shariat, S. Gazor, and D. Redfearn, "Bipolar intracardiac electrogram active interval extraction during atrial fibrillation," *IEEE Transactions on Biomedical Engineering*, vol. 64, no. 9, pp. 2122-2133, 2017.

[6] A. Verma, P. Novak, L. Macle, B. Whaley, M. Beardsall, Z. Wulffhart, and Y. Khaykin, "A prospective, multicenter evaluation of ablating complex fractionated electrograms (CFEs) during atrial fibrillation (AF) identified by an automated mapping algorithm: acute effects on AF and efficacy as an adjuvant strategy," Heart Rhythm, vol. 5, no. 2, pp. 198-205, 2008.

[7] K. Nademanee, M. Schwab, J. Porath, and A. Abbo, "How to perform electrogram-guided atrial fibrillation ablation," Heart Rhythm, vol. 3, no. 8, pp. 981-984, 2006.

[8] F. Atienza, J. Almendral, J. Jalife, S. Zlochiver, R. Ploutz-Snyder, E. G. Torrecilla, A. Arenal, J. Kalifa, F. Fernández-Avilés, and O. Berenfeld, "Real-time dominant frequency mapping and ablation of dominant frequency sites in atrial fibrillation with left-to-right frequency gradients predicts long-term maintenance of sinus rhythm," Heart Rhythm, vol. 6, no. 1, pp. 33-40, 2009.

[9] F. Atienza, J. Almendral, J. M. Ormaetxe, A. Moya, J. D. Mart´ inez-Alday, A. Hernández-Madrid, E. Castellanos, F. Arribas, M. A. Arias, L. Tercedor et al., "Comparison of radiofrequency catheter ablation of drivers and circumferential pulmonary vein isolation in atrial fibrillation: a noninferiority randomized multicenter radar-af trial," Journal of the American College of Cardiology, vol. 64, no. 23, pp. 2455-2467, 2014.

[10] M. Porter, W. Spear, J. G. Akar, R. Helms, N. Brysiewicz, P. Santucci, and D. J. Wilber, "Prospective study of atrial fibrillation termination during ablation guided by automated detection of fractionated electrograms," Journal of cardiovascular electrophysiology, vol. 19, no. 6, pp. 613-620, 2008.

[11] J. W. Jarman, T. Wong, P. Kojodjojo, H. Spohr, J. E. Davies, M. Roughton, D. P.
Francis, P. Kanagaratnam, M. D. O'NEILL, V. Markides et al., "Organizational index mapping to identify focal sources during persistent atrial fibrillation," Journal of cardiovascular electrophysiology, vol. 25, no. 4, pp. 355-363, 2014.

[12] M. Haissaguerre, M. Hocini, A. Denis, A. J. Shah, Y. Komatsu, S. Yamashita, M. Daly, S. Amraoui, S. Zellerhoff, M.-Q. Picat et al., "Driver domains in persistent atrial fibrillation," Circulation, pp. 530-538, 2014.

[13] R. F. Berntsen, T. F. Håland, R. Skårdal, and T. Holm, "Focal impulse and rotor modulation as a stand-alone procedure for the treatment of paroxysmal atrial fibrillation: A within-patient controlled study with implanted cardiac monitoring," Heart Rhythm, vol. 13, no. 9, pp. 1768-1774, 2016.

[14] C. A. Morillo, A. Verma, S. J. Connolly, K. H. Kuck, G. M. Nair, J. Champagne, L. D. Sterns, H. Beresh, J. S. Healey, and A. Natale, "Radiofrequency ablation vs antiarrhythmic drugs as first-line treatment of paroxysmal atrial fibrillation (raaft-2): a randomized trial," Jama, vol. 311, no. 7, pp. 692-700, 2014.

[15] A. Verma, C.-y. Jiang, T. R. Betts, J. Chen, I. Deisenhofer, R. Mantovan, L. Macle, C. A. Morillo, W. Haverkamp, R. Weerasooriya et al., "Approaches to catheter ablation for persistent atrial fibrillation," New England Journal of Medicine, vol. 372, no. 19, pp. 1812-1822, 2015.

[16] J. Ng, A. H. Kadish, and J. J. Goldberger, "Effect of electrogram characteristics on the relationship of dominant frequency to atrial activation rate in atrial fibrillation," Heart Rhythm, vol. 3, no. 11, pp. 1295-1305, 2006.

[17] M. H. Shariat, J. Hashemi, S. Gazor, and D. Redfearn, "Activation detection of intracardiac electrogram during atrial fibrillation based on the variance equality test," in IEEE 28th Canadian Conference on Electrical and Computer Engineering (CCECE), 2015, pp. 387-391.

[18] J. Ng, A. H. Kadish, and J. J. Goldberger, "Technical considerations for dominant frequency analysis," Journal of cardiovascular electrophysiology, vol. 18, no. 7, pp. 757-764, 2007.

[19] A. Verma, D. Lakkireddy, Z. Wulffhart, J. Pillarisetti, D. Farina, M. Beardsall, B. Whaley, D. Giewercer, B. Tsang, and Y. Khaykin, "Relationship between complex fractionated electrograms (CFE) and dominant frequency (DF) sites and prospective assessment of adding DF-guided ablation to pulmonary vein isolation in persistent atrial fibrillation (AF)," Journal of cardiovascular electrophysiology, vol. 22, no. 12, pp. 1309-1316, 2011.

[20] A. M. Climent, I. Hernandez-Romero, M. S. Guillem, N. Montserrat, M. E. Fernández, F. Atienza, and F. Fernandez-Aviles, "High resolution microscopic optical mapping of anatomical and functional reentries in human cardiac cell cultures," in IEEE Computing in Cardiology Conference (CinC), 2016, pp. 233-236.

[21] J. Jalife, O. Berenfeld, and M. Mansour, "Mother rotors and fibrillatory conduction: a mechanism of atrial fibrillation," Cardiovascular research, vol. 54, no. 2, pp. 204-216, 2002.

[22] C. A. M. G. J. Klain, D. L. Jones et al., "Chronic rapid atrial pacing-structural, functional, and electrophysiological characteristics of a new mondel of sustained atrial fibrillation," Circulation, vol. 91, no. 5, pp. 1588-1595, 1995.

[23] S. M. Singh, A. Davila, S. J. Kim, C. Houghtaling, S. R. Dukkipati, and V. Y. Reddy, "Intraprocedural use of Ibutilide to organize and guide ablation of complex fractionated atrial electrograms: Preliminary assessment of a modified step-wise approach to ablation of persistent atrial fibrillation," Journal of cardiovascular electrophysiology, vol. 21, no. 6, pp. 608-616, 20.

The invention claimed is:

1. A method for detecting an abnormality in wavefront propagation during cardiac atrial fibrillation in a subject, comprising:

collecting intracardiac electrograms (IEGMs) via two or more electrodes of a catheter moved to a plurality of different locations in a sampled region of a subject's heart;

preprocessing and combining the IEGMs of the two or more electrodes to obtain a combined preprocessed IEGM;

extracting one or more regional feature from the combined preprocessed IEGM;

using time-frequency or time-scale analysis of the one or more regional feature to detect spatiotemporal heterogeneity in the one or more regional feature and a change in wavefront dynamics;

wherein spatiotemporal heterogeneity in the one or more regional feature and wavefront dynamics in the sampled region indicate an abnormality in wavefront propagation in the subject's heart; and outputting a result including a location of sources of cardiac atrial fibrillation in the subject's heart.

2. The method of claim 1, wherein the preprocessing includes extracting one or more of electrogram active interval envelope, number of baseline occurrence (NO), isoelectric line portion, instantaneous power, and Shannon entropy from the IEGMs of the two or more electrodes.

3. The method of claim 1, wherein combining the preprocessed IEGMs comprises using weighted averaging.

4. The method of claim 1, further comprising signal exclusion.

5. The method of claim 4, wherein signal exclusion comprises one or more of exclusion of a physiologically irrelevant signal, exclusion of electrodes with low signal to noise ratio, and exclusion of an electrogram collected at a selected distance from the atrial surface.

6. The method of claim 1, further comprising outputting the result graphically.

7. The method of claim 6, wherein outputting the result comprises colour coding on a three-dimensional (3D) map of the sampled region.

8. The method of claim 1, wherein the one or more regional feature comprises regional dominant frequency (RDF).

9. The method of claim 8, wherein detecting a change in wavefront dynamics comprises:

determining an instantaneous RDF (iRDF) corresponding to a short time window; and identifying a wave break (WB) in the iRDF.

10. The method of claim 9, comprising identifying a WB based on one or more of:

a drop in iRDF that is at least $f_{th0}$ Hz below the RDF;

a drop in iRDF that is below $f_{th1}$ Hz; and a duration of at least $T_{th}$ ms;

where $f_{th0}$, $f_{th1}$, $T_{th}$ are user defined values.

11. The method of claim 8, comprising determining the RDF based on using an intracardiac electrogram data segment of at least four seconds duration.

12. The method of claim 8, comprising detecting a change in wavefront dynamics relative to the RDF for the sampled region by selecting a short time window of 0.5-3.0 s.

13. The method of claim 8, comprising detecting a change in wavefront dynamics relative to the RDF for the sampled region by selecting a short time window of 2 s or less.

14. The method of claim 1, wherein the abnormality in wavefront propagation in the sampled region identifies a source of cardiac atrial fibrillation in the subject's heart.

15. The method of claim 14, comprising using the source of cardiac atrial fibrillation to determine a location of ablation therapy in the subject.

16. The method of claim 1, further comprising:

determining wave break rate (WBR) to characterize wavefront propagation;

wherein WBR is determined based on an IEGM data segment of at least 25 seconds duration.

17. The method of claim 1, further comprising:

determining a wave break measure to characterize wavefront propagation;

wherein the wave break measure is selected from a WBR that describes a number of WBs per second, a longest WB duration throughout a recording time, average or shortest time between consecutive WBs, or WB duration percentage;

wherein WB duration percentage is the total WB duration divided by IEGM segment duration.

18. The method of claim 1, further comprising:

displaying a colour-coded map to highlight one or more critical site;

wherein a critical site is characterized by at least one of a site with high RDF and low WBR, a site with high WBR and low amplitude, and a site with WBR higher than a selected threshold.

19. The method of claim 1, comprising using time-frequency analysis of the one or more regional feature to detect spatiotemporal heterogeneity in the one or more regional feature and a change in wavefront dynamics.

20. The method of claim 1, comprising using time-scale analysis of the one or more regional feature to detect spatiotemporal heterogeneity in the one or more regional feature and a change in wavefront dynamics.

21. The method of claim 1, comprising using time-frequency and time-scale analysis of the one or more regional feature to detect spatiotemporal heterogeneity in the one or more regional feature and a change in wavefront dynamics.

22. Programmed media for use with a processor, comprising:

a code stored on non-transitory storage media compatible with the processor, the code containing instructions to direct the processor to:

collect intracardiac electrograms (IEGMs) via two or more electrodes of a catheter moved to a plurality of different locations in a sampled region of a subject's heart;

preprocess and combine the IEGMs of the two or more electrodes to obtain a combined preprocessed IEGM;

extract one or more regional feature from the combined preprocessed IEGM;

use at least one of time-frequency and time-scale analysis of the one or more regional feature to detect spatiotemporal heterogeneity in the one or more regional feature and a change in wavefront dynamics;

wherein spatiotemporal heterogeneity in the regional feature and wavefront dynamics in the sampled region indicate an abnormality in wavefront propagation in the subject's heart; and output a result including a location of sources of cardiac atrial fibrillation in the subject's heart.

* * * * *